(12) United States Patent
Ishii et al.

(10) Patent No.: US 11,058,758 B2
(45) Date of Patent: Jul. 13, 2021

(54) TH1-INDUCING ADJUVANT COMPRISING COMBINATION OF DIFFERENT NUCLEIC ACID ADJUVANTS, AND USE OF SAME

(71) Applicant: National Institutes of Biomedical Innovation, Health and Nutrition, Ibaraki (JP)

(72) Inventors: Ken Ishii, Ibaraki (JP); Etsushi Kuroda, Suita (JP); Burcu Temizoz, Suita (JP)

(73) Assignee: National Institutes of Biomedical Innovation, Health and Nutrition, Ibaraki (JP)

( * ) Notice: Subject to any disclaimer, the term of this patent is extended or adjusted under 35 U.S.C. 154(b) by 197 days.

(21) Appl. No.: 15/528,002

(22) PCT Filed: Mar. 20, 2015

(86) PCT No.: PCT/JP2015/001564
§ 371 (c)(1),
(2) Date: May 18, 2017

(87) PCT Pub. No.: WO2016/079899
PCT Pub. Date: May 26, 2016

(65) Prior Publication Data
US 2017/0319680 A1 Nov. 9, 2017

(30) Foreign Application Priority Data

Nov. 20, 2014 (JP) .............................. JP2014-235934

(51) Int. Cl.
*A61K 39/12* (2006.01)
*A61K 39/39* (2006.01)
*A61K 45/00* (2006.01)
*A61K 31/7088* (2006.01)
*A61K 31/7084* (2006.01)
*A61K 31/352* (2006.01)
*A61K 39/00* (2006.01)

(52) U.S. Cl.
CPC ............ *A61K 39/12* (2013.01); *A61K 31/352* (2013.01); *A61K 31/7084* (2013.01); *A61K 31/7088* (2013.01); *A61K 39/39* (2013.01); *A61K 45/00* (2013.01); *A61K 39/00* (2013.01); *A61K 2039/525* (2013.01); *A61K 2039/53* (2013.01); *A61K 2039/55561* (2013.01); *A61K 2039/575* (2013.01)

(58) Field of Classification Search
CPC ...................................................... A61K 39/12
USPC ...................................................... 424/278.1
See application file for complete search history.

(56) References Cited

U.S. PATENT DOCUMENTS

| 2010/0130425 A1* | 5/2010 | Stenzel-Poore ........ A61K 31/00 514/1.1 |
| 2012/0219571 A1* | 8/2012 | Vollmer .................. A61P 37/00 424/184.1 |
| 2016/0136197 A1* | 5/2016 | Schrier .............. A61K 31/7084 424/184.1 |

FOREIGN PATENT DOCUMENTS

| JP | 2003-501460 A | 1/2003 |
| JP | 2008-502713 A | 1/2008 |
| WO | 00/76497 A1 | 12/2000 |
| WO | 2006/049454 A1 | 5/2006 |
| WO | 2013/185052 A1 | 12/2013 |
| WO | 2014/145038 A1 | 9/2014 |

OTHER PUBLICATIONS

Krepler et al., "CpG Oligonucleotides Elicit Antitumor Responses in a Human Melanoma NOD/SCID Xenotransplantation Model," *J. Invest. Dermatol.* 122(2):387-391, 2004. (6 pages).

Temizoz et al., "Synergistic activity of TLR9- and STING-agonists in innate and adaptive Type-II. IFN induction," *The 13th Awaji International Forum on Infection and Immunity in Nara,* Japan, Sep. 23-24, 2014, 2 pages.

Temizoz et al., "Synergistic activity of TLR9- and Sting-agonists in innate and adaptive Type-II IFN induction," *Proceedings of the Japanese Society for Immunology(JSI),* vol. 43, 2014, 4 pages.

Thotathil et al., "Early experience with novel immunomodulators for cancer treatment," *Expert Opin. Investig.Drugs* 16(9):1391-1403, 2007.

Phillips, "Inhibition of DT-diaphorase (NAD(P)H:Quinone Oxidoreductase, EC 1.6.99.2) by 5,6-Dimethylxanthenone-4-acetic Acid (DMXAA) and Flavone-8-acetic Acid (FAA): Implications for Bioreductive Drug Development," *Biochemical Pharmacology* 58:303-310, 1999.

* cited by examiner

*Primary Examiner* — Sean E Aeder
(74) *Attorney, Agent, or Firm* — Seed IP Law Group LLP

(57) ABSTRACT

The present invention provides the induction of novel Th1 response, the induction of cytotoxic T cells and anti-cancer/anti-allergic activity techniques. Provided is a combination of a CpG oligonucleotide and an STING agonist. Also provided is a composition which contains an STING agonist, can be used as a type-I adjuvant, and is characterized in that the STING agonist is administered together with a CpG oligonucleotide. Further provided is an anti-cancer agent comprising a CpG oligonucleotide and is characterized in that the CpG oligonucleotide is administered together with an STING agonist. Still further provided is a composition which contains a CpG oligonucleotide and can be used for reducing or eliminating the IgE-inducing activity of an STING agonist.

8 Claims, 19 Drawing Sheets

Specification includes a Sequence Listing.

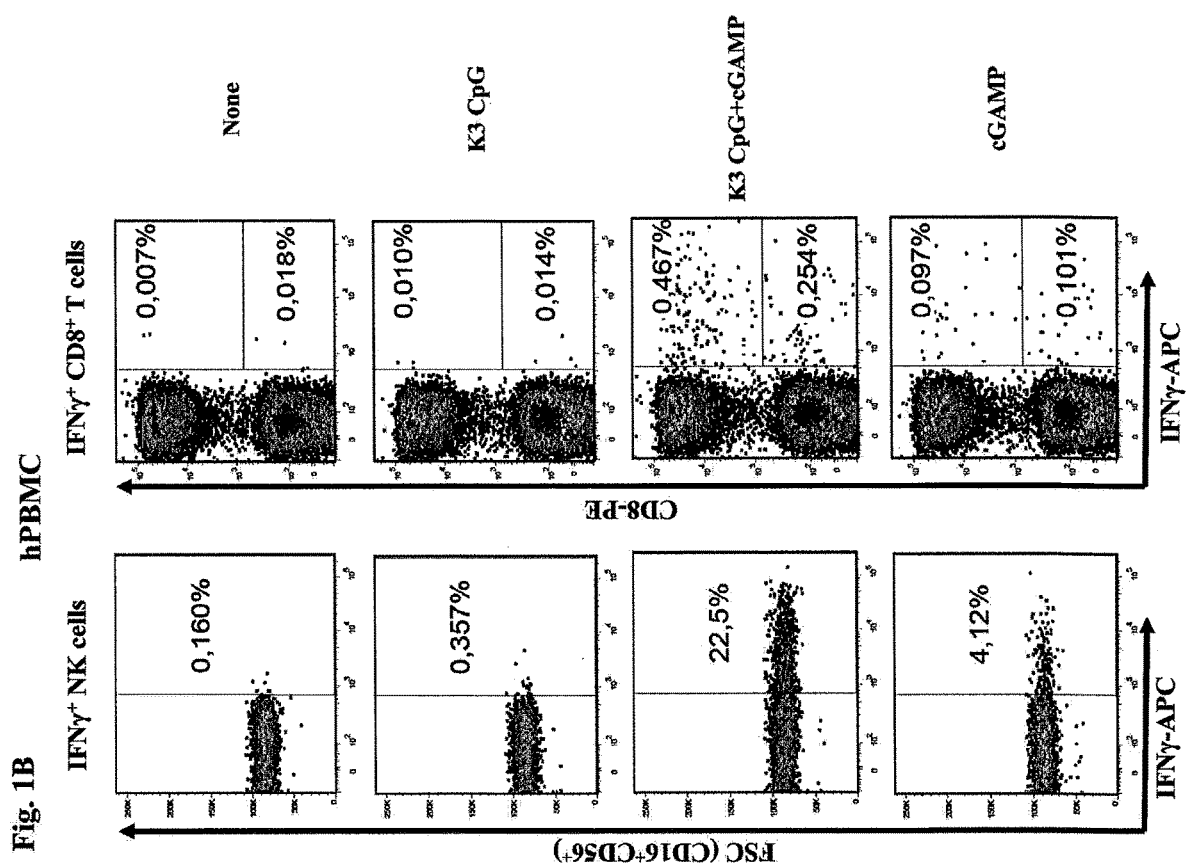

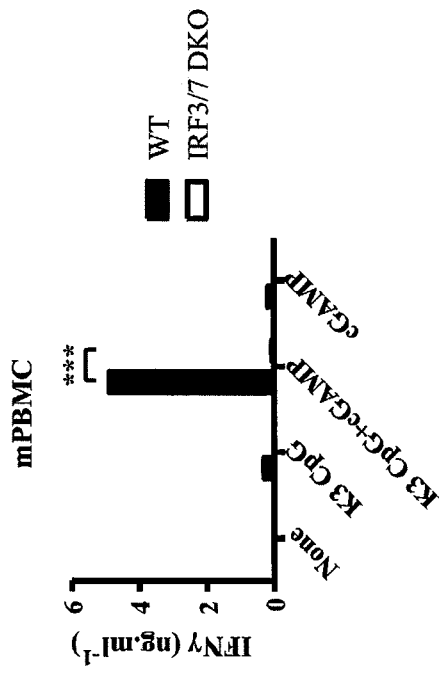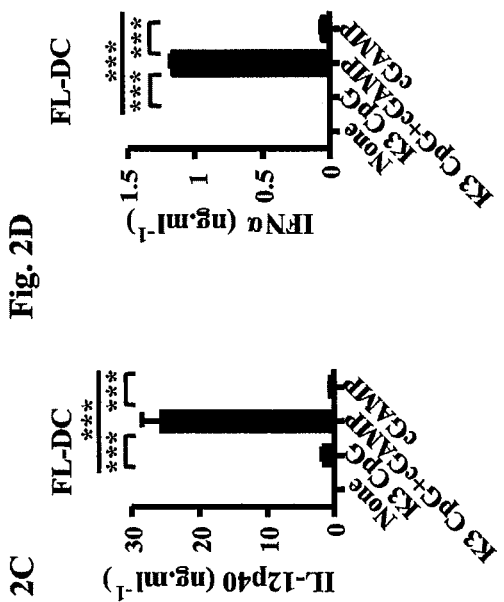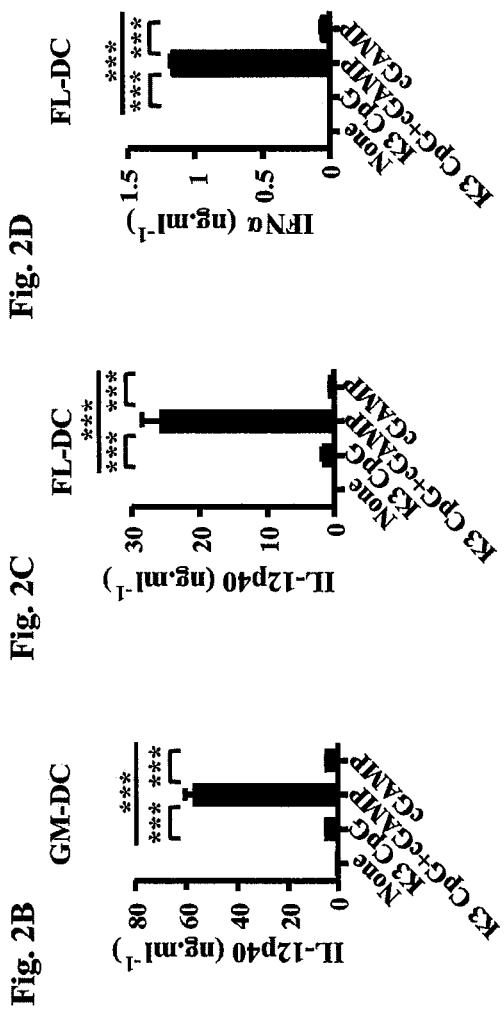
Figure 2

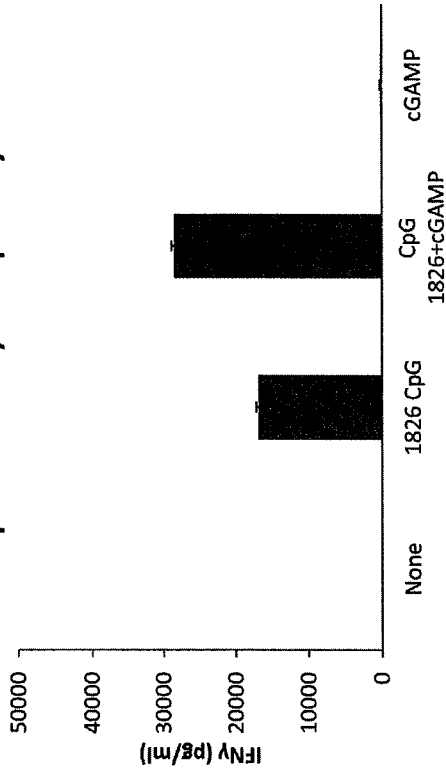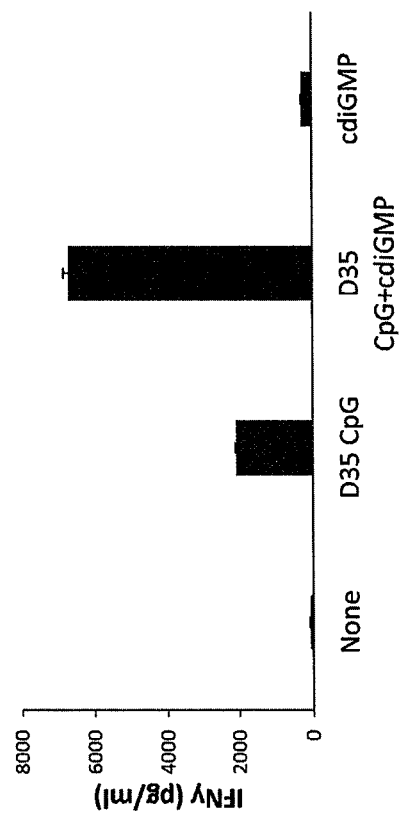
Fig. 12

TH1-INDUCING ADJUVANT COMPRISING COMBINATION OF DIFFERENT NUCLEIC ACID ADJUVANTS, AND USE OF SAME

TECHNICAL FIELD

Statement Regarding Sequence Listing

The Sequence Listing associated with this application is provided in text format in lieu of a paper copy, and is hereby incorporated by reference into the specification. The name of the text file containing the Sequence Listing is 690188 404USPC SEQUENCE LISTING.txt. The text file is 1 KB, was created on May 16, 2017, and is being submitted electronically via EFS-Web.

The present invention relates to the immunological field. More specifically, the present invention relates to a novel Th1-including adjuvant and uses thereof.

BACKGROUND ART

An adjuvant is an immunopotentiator that is added to enhance the effect of a vaccine. With the recent development in immunology, the action mechanism of adjuvants has been gradually elucidated. Recently, various immunoregulatory properties of adjuvants are expected to be applied in the prevention or therapy of not only infections, but also allergies, cancer, and autoimmune diseases.

Many vaccine adjuvants have been developed, mainly to induce antibody production (humoral immunity) up to this point. Many of the current adjuvants, including alum adjuvants are therefore humoral immunity inducing adjuvants called Th2 adjuvants (type II adjuvants). However, induction of cell-mediated immunity is more important than humoral immunity in the prevention or therapy of cancer or allergies. Such adjuvants are called Th1 adjuvants (type I adjuvants) (FIG. 9).

While many candidate substances for Th1 adjuvants have been reported, CpG oligonucleotides (CpG ODN) are considered the most effective. CpG ODN is demonstrated to be effective as a vaccine adjuvant for cancer or infection, but currently a more effective CpG ODN is being developed/improved (Non Patent Literatures 1 and 2). If an effective and improved CpG ODN can be developed, this would more likely be applied to cancer or allergy therapy, more than ever.

CITATION LIST

Non Patent Literature

[NPL 1] Tougan, T. TLR9 adjuvants enhance immunogenicity and protective efficacy of the SE36/AHG malaria vaccine in nonhuman primate models. Hum Vaccin Immunother. 2013, 9(2): 283-90.

[NPL 2] Kobiyama, K. et. al. Nonagonistic dectin-1 ligand transforms CpG into a multitask nanoparticulate TLR9 agonist. Proc Natl Acad Sci USA. 2014, 111(8): 3086-91

SUMMARY OF INVENTION

Solution to Problem

The inventors analyzed induction of a Th1 response, induction of cytotoxic T cells, and anticancer action/anti-allergy action by a combination of CpG ODN and a STING agonist. The inventors discovered that the specific combination of the invention can be used in the induction of Th1 immune responses (FIG. 1A), application to the prevention/therapy of cancer (FIG. 5), and application to the prevention/therapy of allergies (FIG. 8). The inventors have also revealed that the combination enables switching between a type I immune response (cell-mediated immunity) and a type II immune response (humoral immunity) (FIG. 11).

The inventors attempted to overcome issues for each of K3 CpG and cGAMP by combining K3 CpG and 3'3'-cGAMP. The inventors investigated immunological characteristics, efficacy as a vaccine adjuvant, potential of this combination as antitumor immunotherapy, and in vitro and in vivo action mechanisms. Human and mouse PBMCs were used to analyze the effect of combining K3 CpG and cGAMP in vitro. Furthermore, the effect of the combination was analyzed in vivo by measuring the induction of antigen specific T cell and B cell responses after combination of immunization through an immunization model. Finally, the inventors evaluated the ability to suppress tumor growth of combined K3 CpG and cGAMP in a mouse tumor model. The results obtained by the inventors indicate that the combination of K3 CpG and cGAMP makes a potent type 1 adjuvant and a promising immunotherapeutic agent against cancer.

The inventors have discovered that: the combination of CpG ODN and STING agonist synergistically induces a Th1 immune response (FIG. 10); IgE production induced as a side effect of a STING agonist is suppressed; a Th1 response requires an MyD88 signal and a STING-type I interferon signal; concomitant administration of CpG ODN and a STING agonist effectively suppresses cancer cell growth in vivo in cancer-bearing model mice (FIG. 5); and human peripheral blood mononuclear cells (PBMC) are stimulated to strongly induce an indicator of a Th1 response, IFN-γ (FIG. 1A).

Various STING agonists were evaluated. Each of endogenous STING agonist 2' 3'-cGAMP, microbe-derived 3'3'-cGAMP, c-di-GMP, and synthetic STING agonist DMXAA, when administered with CpG into a mouse, was recognized as inducing a Th1 immune response.

These results revealed that a combination of a CpG ODN-originated TLR9 signal and a STING-type T interferon signal is an important signal for inducing a potent Th1 immune response. It was also suggested that the same effect would be found in humans. It is understood that use thereof as an adjuvant enables vaccine therapy of cancer or allergy, which had been difficult in the past.

Thus, the present invention provides a method of inducing a Th1 adjuvant that is more effective than conventional adjuvants, and a novel therapeutic method for cancer or allergy by a combination of CpG ODN and another nucleic acid adjuvant (STING agonist). The present invention relates to a marker for identifying a Th1 response induced by a combination of adjuvants, such as a signaling system agent or an expression product thereof associated with induction of a Th1 response, induction of a cytotoxic T cell, and anticancer action/anti-allergy action by a combination of CpG ODN and a STING agonist, or a fragment or a derivative thereof, detection agent, inhibitor, and a composition for preventing or treating cancer or allergies.

In this manner, agonists for TLR9 and a stimulator of interferon genes (STING) (STING agonist or STING ligand) can function as a vaccine adjuvant. However, currently available CpG ODN (type K/B) weakly induces IFN, and a STING agonist induces a type 2 immune response to limit potential therapeutic applications. In the present invention, the inventors discovered that a potent synergistic action is exhibited between a TLR9-agonist and a STING-agonist. These were combined to successfully make an effective type 1 adjuvant and an anticancer agent. The in vitro studies of the inventors suggest that a synergistic effect between a STING agonist (e.g., cGAMP) and CpG ODN (e.g., K3), which ultimately produces IFNγ (type II IFN) of NK cells, is regulated separately by IRF3/7, STING, and MyD88 due to the simultaneous action of IL-12 and type I IFN. The in vivo immunization model of the inventors revealed that the combination of cGAMP and CpG ODN functions as a potent type 1 adjuvant, capable of inducing a strong Th1 response, as shown by the promotion of $CD8^+$ T cell responses in addition to the production of T-cell derived IFNγ and a highly antigen-specific IgG2c antibody response. In the mouse tumor model of the inventors, intratumor injection of both CpG ODN and cGAMP significantly reduced the tumor size relative to treatment using them individually, and CpG ODN and cGAMP functioned as an anticancer agent free of antigens. Thus, the combination of CpG ODN and a STING agonist provides therapeutic application as a potent type II IFN inducing agent. Thus, the present invention provides the following.

<Invention Series Focused on "Combination">

(1) A combination of a CpG oligonucleotide and a STING agonist.
(2) The combination of item 1 for use as a type I adjuvant.
(3) The combination of item 1 or 2 for suppressing IgE inducing action of the STING agonist.
(4) The combination of any one of items 1 to 3, wherein the CpG oligonucleotide is a type K/B oligonucleotide.
(5) The combination of any one of items 1 to 4, wherein the CpG oligonucleotide is a CpG oligonucleotide selected from the group consisting of K3CpG (SEQ ID NO: 1=5'-atcgactatcgagagttctc-3'), CpG 1826 (SEQ ID NO: 2=5'-tccatgacgttcctgacgtt-3'), and D35 CpG (SEQ ID NO: 3=5'-ggtgcatcgatgcagggggg-3').
(6) The combination of any one of items 1 to 5, wherein the STING agonist is a STING agonist selected from cGAMP, 3'3'-cGAMP, c-di-GAMP, c-di-AMP, 2'3'-cGAMP, and DMXAA.
(7) The combination of any one of items 1 to 6 for use as an anticancer agent.
(8) The combination of item 7, wherein the anticancer agent is targeted for cancer selected from lymphoma and melanoma.
(9) The combination of any one of items 1 to 8 for reducing or eliminating a type II immune response and expressing or enhancing a type I immune response.
(10) The combination of anyone of items 1 to 9 for inducing interferon γ (IFN-γ).
(11) The combination of any one of items 1 to 10 for use as a vaccine adjuvant.
(A1) A method of treating or providing prevention to a subject, comprising administering a combination of an effective amount of a CpG oligonucleotide and a STING agonist to the subject.
(A2) The method of item A1, wherein the combination is used as a type I adjuvant.
(A3) The method of item A1 or A2, wherein the CpG oligonucleotide is provided at an effective amount to suppress IgE inducing action of the STING agonist.
(A4) The method of any one of items A1 to A3, wherein the CpG oligonucleotide is a type K/B oligonucleotide.
(A5) The method of any one of items A1 to A4, wherein the CpG oligonucleotide is a CpG oligonucleotide selected from the group consisting of K3 CpG (SEQ ID NO: 1=5'-atcgactatcgagagttctc-3'), CpG 1826 (SEQ ID NO: 2=5'-tccatgacgttcctgacgtt-3'), and D35 CpG (SEQ ID NO: 3=5'-ggtgcatcgatgcagggggg-3').
(A6) The method of any one of items A1 to A5, wherein the STING agonist is a STING agonist selected from cGAMP, 3'3'-cGAMP, c-di-GAMP, c-di-AMP, 2'3'-cGAMP, and DMXAA.
(A7) The method of any one of items A1 to A6, wherein the treating or providing prevention is targeted for cancer.
(A8) The method of item A7, wherein the cancer is selected from lymphoma and melanoma.
(A9) The method of any one of items A1 to A8, wherein the treating or providing prevention reduces or eliminates a type II immune response and expresses or enhances a type I immune response.
(A10) The method of any one of items A1 to A9, wherein the treating or providing prevention induces interferon γ (IFN-γ).
(A11) The method of any one of items A1 to A10, wherein the combination is used as a vaccine adjuvant.

<Invention Series Emphasizing the Application of STING Agonist Itself as Type I Adjuvant Formulation>

(12) A combination for use as a type I adjuvant, comprising a STING agonist, wherein the STING agonist is administered with a CpG oligonucleotide.
(13) The composition of item 12, having one or more features of items 2 to 11.
(A12) A method of exerting a type I adjuvant effect of a STING agonist, comprising administering the STING agonist with a CpG oligonucleotide.
(A13) The method of item A12 having one or more features of items 2 to 11 or A2 to A11.

<Invention Series Emphasizing Effect of Enhancing Type I Adjuvant Formulation of STING Agonist on CpG>

(14) An action enhancing agent for a type I adjuvant of a CpG oligonucleotide, comprising a STING agonist.
(15) The action enhancing agent of item 14 having one or more features of items 2 to 11.
(A14) A method of enhancing action of a type I adjuvant of a CpG oligonucleotide, comprising administering the CpG oligonucleotide with a STING agonist.
(A15) The method of item A14 having one or more features of items 2 to 11 or A2 to A11.

<Invention Series Emphasizing Aspect of STING Agonist as an Anticancer Agent>

(16) An anticancer agent comprising a STING agonist, wherein the STING agonist is administered with a CpG oligonucleotide.
(17) The anticancer agent of item 16 having one or more features of items 2 to 11.
(A16) A method of treating or preventing cancer, the method comprising:
administering an anticancer agent comprising a STING agonist with a CpG oligonucleotide.
(A17) The method of item A16 having one or more features of items 2 to 11 or A2 to A11.

<Invention Series Emphasizing Aspect of CpG Oligonucleotide as Anticancer Agent>

(18) An anticancer agent comprising a CpG oligonucleotide, wherein the CpG oligonucleotide is administered with a STING agonist.
(19) The anticancer agent of item 18 having one or more features of items 2 to 11.
(A18) A method of treating or preventing cancer, wherein the method comprises administering an anticancer agent comprising a CpG oligonucleotide with a STING agonist.

(A19) The method of item A18 having one or more features of items 2 to 11 or A2 to A11.

<Claim Series Emphasizing Suppression of Allergy (IgE) Inducing Action of STING Agonist with CpG>

(20) A composition for reducing or eliminating IgE inducing action of a STING agonist, comprising a CpG oligonucleotide.

(21) The composition of item 20, wherein allergy inducing action of the STING agonist is reduced or eliminated.

(22) The composition of item 20 or 21 having one or more features of items 2 to 11.

(A20) A method of reducing or eliminating IgE inducing action of a STING agonist, wherein the method comprises administering a CpG oligonucleotide when using the STING agonist.

(A21) The method of item A20, wherein allergy inducing action of the STING agonist is reduced or eliminated.

(A22) The method of item A20 or A21 having one or more features of items 2 to 11 or A2 to A11.

In the present invention, one or more features described above are intended to be provided not only as the explicitly described combinations, but also as other combinations thereof.

The additional embodiments and advantages of the present invention are recognized by those skilled in the art by reading the following disclosure in detail, as needed.

Advantageous Effects of Invention

The present invention provides a novel adjuvant inducing a Th1 immune response, which had been difficult to accomplish, and information on inducing signals thereof. Many of the current adjuvants are Th2 adjuvants inducing antibody production. Meanwhile, such adjuvants were unsuited for vaccine therapy of cancer or allergies. Furthermore, STING agonists induce IgE as a side effect. Thus, there is a risk of inducing allergic inflammation. However, the present invention can induce a potent Th1 adjuvant effect while suppressing IgE induction by simply combining two types of adjuvants. Further, STING agonists themselves, including DMXAA, function as a TH2 adjuvant that activates humoral immunity as in alum adjuvants. Thus, a STING agonist, used as a platform, can be used as a conventional humoral immunity inducing Th2 adjuvant when directly used, or as a potent cell-mediated immunity inducing Th1 adjuvant when combined with CpG ODN (FIG. 11). Such a highly versatile adjuvant, which can be used for diseases that are qualitatively different, is unprecedented, thus having a technical and economical ripple effect as a next-generation adjuvant.

BRIEF DESCRIPTION OF DRAWINGS

FIG. 1A shows results for, from the left, no adjuvant, K3 CpG, K3 CpG+cGAMP, and cGAMP. The vertical axis indicates the IFNγ concentration of culture supernatant (ng/ml). K3 CpG and cGAMP (TLR9-agonist and STING-agonist, respectively) synergistically induce the production of congenital IFNγ by NK cells. Human PBMCs from two healthy donors were incubated for 24 hours with K3 CpG (10 μg/ml), cGAMP (10 μM), or K3 CpG+cGAMP to measure the IFNγ concentration of the supernatant by ELISA. The data is a representation of at least two independent experiments and is shown as the average of the two groups+SD; *p<0.05, ** p<0.01 (one-way ANOVA including Bonferroni multiple comparison test).

FIG. 1B shows results of flow cytometry analysis. FIG. 1B shows results for, from the top row, no adjuvant, K3 CpG, K3 CpG+cGAMP, and cGAMP. The vertical axis of the panel of the left column indicates the forward scattering (FSC) intensity of CD16 positive CD56 positive natural killer cells (NK cells), and the horizontal axis indicates the fluorescence right column indicates the fluorescence intensity of CD8-PE, and the horizontal axis indicates the fluorescence intensity of IFNγ-APC. K3 CpG and cGAMP (TLR9-agonist and STING-agonist, respectively) synergistically induce the production of congenital IFNγ by NK cells. Human PBMCs from three healthy donors were stimulated for 16 hours with K3 CpG, cGAMP, or K3 CpG+cGAMP, and stimulated in the presence of Brefeldin A for the last 4 hours. After stimulation, the cells were analyzed by flow cytometry to detect IFNγ producing cells. The graphs indicate the percentage of IFNγ producing $CD3^+CD8^+$ T cells, $CD3^+CD8^-$ T cells (including $CD4^+$ T cells), and $CD3^-CD56^+CD16^+$ NK cells.

FIG. 1C shows results for, from the left group, no adjuvant, K3 CpG, K3 CpG+cGAMP, and cGAMP. For each group, FIG. 1C shows results for, from the left, isotype control, α-type I IFN, α-IL-12/23p40, and α-type I IFN+α-IL-12/23p40. K3 CpG and cGAMP (TLR9-agonist and STING-agonist, respectively) synergistically induce the production of congenital IFNγ by NK cells. Human PBMCs from two healthy donors were treated with 5 μg/ml isotype control, type-I IFN neutralizing antibody, IL-12/23p40 neutralizing antibody, or type-I IFN+IL-12/23p40 neutralizing antibody for 30 seconds prior to stimulation for 24 hours with K3 CpG, cGAMP, or K3 CpG+cGAMP. IFNγ production was measured by ELISA. The data is a representation of at least two independent experiments and is shown as the average of two groups+SD; *p<0.05, ** p<0.01 (one-way ANOVA including Bonferroni multiple comparison test).

FIG. 2A shows the concentration of IFNγ produced in the supernatant of a mouse PBMC culture. FIG. 2A shows results for, from the left group, no adjuvant, K3 CpG, K3 CpG+cGAMP, and cGAMP. The left side of each group shows results for those derived from wild-type mice and the right side shows results for those derived from IRF3/7 DKO mice. The vertical axis indicates the IFNγ concentration in the culture supernatant (ng/ml). The combination of K3 CpG and cGAMP leads to the synergistic induction of congenital IFNγ in mPBMCs in an IRF3/7 dependent manner and the production of IFNα and IL-12 by dendritic cells. Mouse PBMCs derived from wild-type mice and IRF3/7 DKO mice were stimulated for 24 hours with K3 CpG, cGAMP, or K3 CpG+cGAMP to measure IFNγ production with ELISA. The data is a representation of at least two independent experiments and is shown as the average of the two groups+SEM; *** p<0.001 (Student's t-test.

FIG. 2B shows the concentration of IL-12p40 produced by DM-DC. FIG. 2B shows, from the left, no adjuvant, K3 CpG, K3 CpG+cGAMP, and cGAMP. The vertical axis indicates the concentration of IL-12p40 (ng/ml). The combination of K3 CpG and cGAMP leads to the synergistic induction of congenital IFNγ in mPBMCs in an IRF3/7 dependent manner, and the production of IFNα and IL-12 by dendritic cells. GM-DCs were stimulated for 24 hours with K3 CpG, cGAMP, or K3 CpG+cGAMP to measure the production of IL-12p40 by ELISA. The data is a representation of at least two independent experiments and is shown as the average of the two groups+SD; *** p<0.001 (one-way ANOVA including Bonferroni multiple comparison test).

FIG. 2C shows the concentration of IL-12p40 produced by FL-DC. FIG. 2C shows the results for, from the left, no adjuvant, K3 CpG, K3 CpG+cGAMP, and cGAMP. The vertical axis indicates the concentration of IL-12p40 (ng/ml). The combination of K3 CpG and cGAMP leads to the synergistic induction of congenital IFNγ in mPBMCs in an IRF3/7 dependent manner and the production of IFNα and IL-12 by dendritic cells. FL-DCs were stimulated for 24 hours with K3 CpG, cGAMP, or K3 CpG+cGAMP to measure the production of IL-12p40 by ELISA. The data is a representation of at least two independent experiments and is shown as the average of two groups+SD; *** p<0.001 (one-way ANOVA including Bonferroni multiple comparison test).

FIG. 2D shows the concentration of IL-12p40 produced by FL-DCs. FIG. 2D shows the results for, from the left, no adjuvant, K3 CpG, K3 CpG+cGAMP, and cGAMP. The vertical axis indicates the concentration of INFα (ng/ml). The combination of K3 CpG and cGAMP leads to the synergistic induction of congenital IFNγ in mPBMCs in an IRF3/7 dependent manner and the production of IFNα and IL-12 by dendritic cells. FL-DCs were stimulated for 24 hours with K3 CpG, cGAMP, or K3 CpG+cGAMP to measure the production of IFNα by ELISA. The data is a representation of at least two independent experiments and is shown as the average of two groups+SD; *** p<0.001 (one-way ANOVA including Bonferroni multiple comparison test).

FIG. 3A shows the results for, from the left, no adjuvant, K3 CpG, K3 CpG+ 3'3'-cGAMP, 3'3'-cCAMP, K3 CpG+c-di-GMP, c-di-GMP, K3 CpG+2'3'-cGAMP, and 2'3'-cGAMP. The vertical axis indicates the concentration of IFNγ in the culture supernatant (ng/ml). A combination of a TLR9-agonist and a STING-agonist is a potent type 1 adjuvant that suppresses type 2 immune responses in vivo. Mouse PBMCs were stimulated for 24 hours with K3 CpG (10 µg/ml), STING-agonist (10 µM), or K3 CpG+STING agonist to measure the production of IFNγ by ELISA. The data is a representation of at least two independent experiments and is shown as the average of the two groups+SEM.

FIG. 4A shows results for, from the left in each group, wild type, Tmem173gt, MyD88 KO, IRF3/7 DKO, and IFNAR KO mice. The synergistic effect of the combination of K3 CpG and cGAMP in induction of antigen-specific IFNγ is dependent on IRF3/7, STING, MyD88, IL-12, and type I IFN signaling. The wild type, Tmem173gt, IRF3/7 DKO, MyD88 KO, and IFNAR KO C57BL/6J mice were immunized via an intramuscular route on day 0 and day 10 with OVA and K3 CpG, cGAMP, or K3 CpG+cGAMP. On day 17, OVA specific sera IgG2c and IgG1 were measured by ELISA. The data is a representation of at least two independent experiments and is shown as the average of two groups+SD; *p<0.05, ** p<0.01, p<0.001 (one-way ANOVA including Bonferroni multiple comparison test).

FIG. 4B shows results for, from the left in each group, wild type, Tmem173gt, MyD88 KO, IRF3/7 DKO, and IFNAR KO mice. The synergistic effect of the combination of K3 CpG and cGAMP in the induction of antigen-specific IFNγ is dependent on IRF3/7, STING, MyD88, IL-12, and type I IFN signaling. The splenocytes were stimulated for 48 hours with OVA. The production of IFNγ was measured by ELISA. The data is a representation of at least two independent experiments and is shown as the average of the two groups+SD; *p<0.05,  p<0.01, *p<0.001 (one-way ANOVA including Bonferroni multiple comparison test).

FIG. 6 shows results for, from the left group, saline, K3 CpG, K3 CpG cGAMP, and cGAMP. The vertical axis indicates the concentration of IFNγ (ng/ml). The combination of K3 CpG and cGAMP induces a potent $CD8^+$ T cell activity in vivo. Mice were immunized via an intramuscular route on day 0 and day 10 with only OVA (n=2), OVA and K3 CpG (n=4), cGAMP (n=4), or K3+cGAMP (n=4). On day 17, the splenocytes were isolated and stimulated for 48 hours with a MHC class I (OVA257) or a MHC class II (OVA323) specific OVA or an OVA peptide. The production of IFNγ was measured by ELISA. The data is a representation of at least two independent experiments; *$p<0.05$, **$p<0.01$ (Student's t-test).

FIG. 8 shows results for, from the left, saline, K3 CpG, cGAMP, and K3 CpG+cGAMP. The vertical axis indicates the concentration of IgE. STING agonists induce IgE, but this is suppressed by combining it with CpG.

FIG. 12 is a diagram showing the synergistic effect of interferon gamma production of a combination of CpG 1826 and 3'3'-cGAMP or a combination of D35 CpG and 3'3'-cGAMPc-di-GMP in splenocytes. The top row shows a combination of CpG 1826 and 3'3'-cGAMP and the bottom row shows a combination of D35 CpG and 3'3'-cGAMPc-di-GMP. Each y axis indicates the quantity of interferon gamma (IFNγ) produced (pg/ml), and the x axis shows results for, from the left, no stimulation, a combination of CpG 1826 and 3'3'-cGAMP, or a combination of D35 CpG and 3'3'-cGAMPc-di-GMP, and 3'3'-cGAMP alone.

DESCRIPTION OF EMBODIMENTS

Figure 1A:
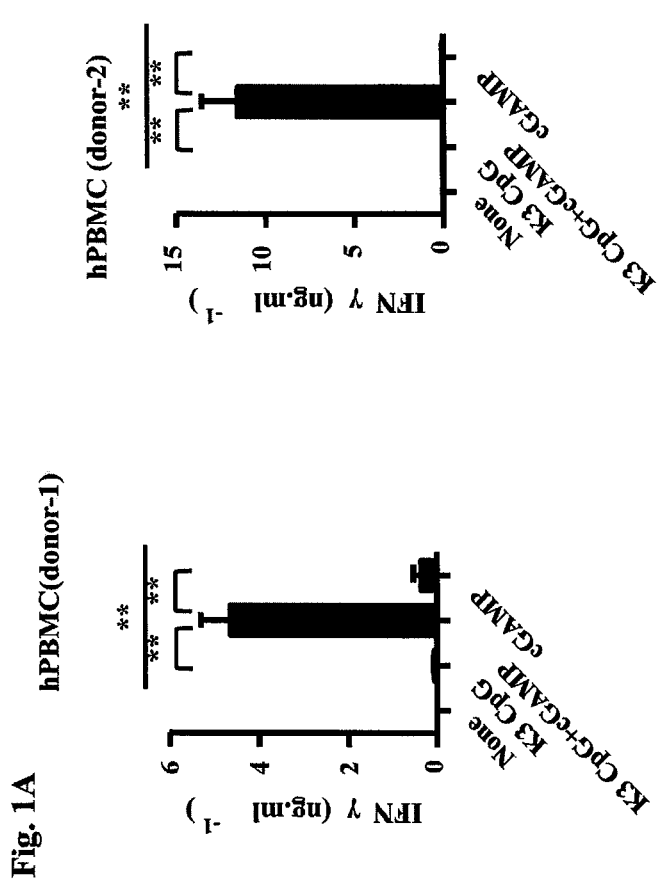
FIG. 1A shows the concentration of IFNγ produced in the supernatant of a human PBMC culture of each donor.

The present invention is disclosed hereinafter while showing the best mode of the invention. Throughout the entire specification, a singular expression should be understood as encompassing the concept thereof in the plural form, unless specifically noted otherwise. Thus, singular articles (e.g., "a", "an", "the", and the like in the case of English) should also be understood as encompassing the concept thereof in the plural form unless specifically noted otherwise. Further, the terms used herein should be understood to be used in the meaning that is commonly used in the art, unless specifically noted otherwise. Thus, unless defined otherwise, all terminologies and scientific technical terms that are used herein have the same meaning as the general understanding of those skilled in the art to which the present invention pertains. In case of a contradiction, the present specification (including the definitions) takes precedence.

The definition of the terms and/or general techniques particularly used herein is explained hereinafter, as appropriate.

As used herein, "CpG oligonucleotide", "CpG oligodeoxynucleotide", "CpG ODN", or "simply "CpG" are interchangeably used, and refer to a polynucleotide, preferably an oligonucleotide, comprising at least one non-methylated CG dinucleotide sequence. An oligonucleotide comprising at least one CpG motif may comprise multiple CpG motifs. As used herein, the phrase "CpG motif" refers to a non-methylated dinucleotide moiety of an oligonucleotide, comprising a cytosine nucleotide and a subsequent guanosine nucleotide. 5-methylcytosine may also be used instead of cytosine.

A CpG oligonucleotide (CpG ODN) is a short (about 20 base pairs) synthetic single-stranded DNA fragment comprising an immunostimulatory CpG motif. A CpG oligonucleotide is a potent agonist of a toll-like receptor 9 (TLR9), which activates dendritic cells (DCs) and B cells to produce type I interferons (IFNs) and inflammatory cytokines (Hemmi, H., et al. Nature 408, 740-745 (2000); Krieg, A. M. Nature reviews. Drug discovery 5, 471-484 (2006).), and acts as an adjuvant of Th1 humoral and cell-mediated immune responses, including cytotoxic T-lymphocyte (CTL) reactions (Brazolot Milian, C. L, Weeratna, R., Krieg, A. M., Siegrist, C. A. & Davis, H. L. Proceedings of the National Academy of Sciences of the United States of America 95, 15553-15558 (1998).; Chu, R. S., Targoni, O. S., Krieg, A. M., Lehmann, P. V. & Harding, C. V. The Journal of experimental medicine 186, 1623-1631 (1997)). In this regard, CpG ODN has been considered a potential immunotherapeutic agent against inflammation, cancer, asthma, and hay fever (Krieg, A. M. Nature reviews. Drug discovery 5, 471-484 (2006); Klinman, D. M. Nature reviews. Immunology 4, 249-258 (2004)).

A CpG oligodeoxynucleotide (CpG ODN) is a synthetic single stranded DNA comprising a non-methylated CpG motif with a immunostimulatory feature due to similarity with a microbial genome, and is recognized by TLR9 in a specific type of natural immune cell [Hartmann et al., J. Immunol. (2000) 164: 944-953; Wagner et al., Trends Immunol. (2004) 25: 1-6]. In ligand binding, TLR9 signals through an adapter molecule myD88 to induce the production of IRF7 dependent type I IFN and NF-κB dependent cytokines [Krieg et al., Nat. Rev. Drug Discov. (2006) 5: 471-84] Furthermore, it is reported that CpG ODN induces a Th1 response due to the type of cytokine induced by CpG ODN in APC in vivo [Krieg et al., Nat. Rev. Drug Discov. (2006) 5: 471-84]. Among different types of CpG ODN, type D CpG ODN strongly induces both type I and type II IFN, but cannot induce B cell activation [Krieg et al., Nat. Rev. Drug Discov. (2006) 5: 471-84; Klinman et al., Nat. Rev. Immunol. (2004) 4:1-10]. Type K CpG ODN (K3 CpG) strongly induces B cell activation to induce IL-6 and antibody production, but they only weakly induce type I and type II IFN. However, type D CpG ODN forms an aggregation, such that only type K CpG can be used for clinical applications [Krieg et al., Nat. Rev. Drug Discov. (2006) 5: 471-84; Klinman et al., Nat. Rev. Immunol. (2004) 4: 1-10].

Pathogen derived agents such as LPS or non-methylated CpG DNA (CpG) (CpG ODN) stimulate natural immune cells that produce cytokines such as type I or type II IFN and IL-12. This is useful in inducing a Th1 response and cell-mediated immunity [Kawai et al., Immunity. (2011) 34: 637-650; Trinchieri et al., Immunol. (2007) 7: 179-190]. IL-12 acts on naïve CD4+ T cells to derive the generation of Th1 and the production of IFNγ [Seder et al., Proc. Natl. Acad. Sci. U.S.A. (1993) 90: 10188-92; Hsieh et al., Science. (1993) 260: 547-579]. In addition, IFNγ producing Th1 cells are the main actors in the induction of type 1 immunity, which are distinguished by high phagocytic activity [Spellberg et al., Clin. Infect. Dis. (2001) 90509: 76-102; Mantovani et al., Curr. Opin. Immunol. (2010) 22: 231-237]. Furthermore, Th1 cells play an important role in the generation of antitumor immunity and are useful in CTL effector functions and suitable activation including IFNγ production [Hung et al., J. Exp. Med. (1998) 188: 2357-68; Vesely et al., Annu. Rev. Immunol. (2011) 29: 235-271]. Thus, agents, CTLs, and NK cells that can induce a strong Th1 response [Vitale et al., Eur. J. Immunol. (2014) 44: 1582-1592] may play an important role in the development of a vaccine adjuvant or immunotherapeutic agent that is effective against intracellular pathogens or cancer. Therefore, they are in immediate demand.

Depending on the difference in backbone modification or surrounding sequences, they are classified into type D/A, type K/B, type C, and type P (Vollmer, J. & Krieg, A. M. Advanced drug delivery reviews 61, 195-204 (2009).) It is suggested that type D/A induces the production of type I interferon mainly from plasmacytoid dendritic cells (called "plasmacytoid DC" or "pDC"), and type K/B induces B cell growth and the production of IgM, IL-6 or the like. Type D/A CpG-DNA strongly induces IFN-α production, but exhibits low pDC maturation inducing activity and no direct immunostimulatory activity to B cells. Type K/B exhibits immunostimulatory activity to B cells, strongly promotes maturation of pDCs, and has high IL-12 inducing capability, but has low IFN-α inducing capability. In type C sequences having repetitive sequences of TCG that are completely thiolated, IFN-α production by pDCs or polyclonal B cell activation is induced.

Type D/A CpG ODN (also called type A, type D or the like and denoted as CpG-A ODN) is an oligonucleotide characterized by a phoshothioate (PS) bond at the 5' and 3' terminuses and by a poly G motif with a palindrom (palindromic structure) CpG containing sequence of phosphodiester (PO) in the middle. Cell uptake is facilitated due to the presence of phosphorothioate (PS) at the 5' and 3' terminuses. CpG type D/A produces a large quantity of interferon α (IFN-α) in pDCs (different feature from CpG type K/B). A potent activation and interferon gamma production are induced thereby in NK cells and γδ T cells. However, B cells are not activated and pDCs are not matured (Krug, A., et al. European journal of immunology 31, 2154-2163 (2001).; and Verthelyi, D., Ishii, K. J., Gursel, M., Takeshita, F. & Klinman, D. M. Journal of immunology 166, 2372-2377 (2001).)

Three other types of ODN consist of a PS backbone.

Type K/B CpG ODN is also called CpG-type B or CpG-type K. All type K/B CpG ODN with one or more CpG motifs without a poly G motif have a phosphorothioate (PS) backbone. Typically, type K/B CpG ODN contains multiple CpG motifs with a non-palindromic structure. Type K/B CpG has weak IFN-α inducing activity (produces nearly none), but is a very potent Th1 adjuvant and a potent B cell response stimulating agent which produces IL-6 and activates and matures pDCs (Verthelyi, D., Ishii, K. J., Gursel, M., Takeshita, F. & Klinman, D. M. Journal of immunology 166, 2372-2377 (2001); and Hartmann, G. & Krieg, A. M. Journal of immunology 164, 944-953 (2000)). Type K/B CpGODN has a function of promoting the survival, activating, and maturing both monocyte derived dendritic cells and pDCs.

Recently developed type C and type P CpG ODN comprise one and two palindromic structure CpG sequences, respectively. Both can activate B cells, like type K CpG ODN, and activate pDCs, like type D CpG ODN. Meanwhile, type C CpG ODN more weakly induces IFN-α production relative to type P CpG ODN (Hartmann, G., et al. European journal of immunology 33, 1633-1641 (2003); Marshall, J. D., et al. Journal of leukocyte biology 73, 781-792 (2003).; and Samulowitz, U., et al. Oligonucleotides 20, 93-101 (2010)).

Type D/K and type P CpG ODN are shown to form a higher order structure i.e., Hoogsteen base pair forming a four parallel strand structure called G-tetrads and Watson-Crick base pair between a cis palindromic structure site and a trans palindromic structure site, respectively, which are required for potent IFN-α production by pDCs (Samulowitz, U., et al. Oligonucleotides 20, 93-101 (2010).; Kerkmann, M., et al. The Journal of biological chemistry 280, 8086-8093 (2005).; and Klein, D. C., Latz, E., Espevik, T. & Stokke, B. T. Ultramicroscopy 110, 689-693 (2010)). Due to the higher order structure, only type K and type C CpG ODN are generally considered usable as immunotherapeutic agents and vaccine adjuvants for humans (Puig, M., et al. Nucleic acids research 34, 6488-6495 (2006); Bode, C., Zhao, G., Steinhagen, F., Kinjo, T. & Klinman, D. M. Expert review of vaccines 10, 499-511 (2011); and McHutchison, J. G., et al. Hepatology 46, 1341-1349 (2007)).

In contrast to type A CpG ODN, type C CpG ODN has a complete phosphorothioate (PS) backbone without a poly G motif, but comprises the type A palindromic sequence of CpG in combination with a stimulatory CpG motif. It is reported from an in vivo study that type C CpG ODN is a very potent Th1 adjuvant.

Type K CpG ODN used in a preferred embodiment in the present invention has a length of 10 nucleotides or longer and comprises the nucleotide sequence set forth in the following formula:

[Chemical 1]

wherein the middle CpG motif (described as CpG) is not methylated, W is A or T, and N1, N2, N3, N4, N5, and N6 may be any nucleotide.

In one embodiment, type K CpG ODN of the invention has a length of 10 nucleotides or longer and comprises the nucleotide sequence of the above-described formula. However, in the above-described formula, the CpG motif of 4 bases in the middle (TCpGW) only needs to be included in the 10 nucleotides. The motif does not necessarily need to be positioned between N3 and N4 in the above-described formula. Further, the N1, N2, N3, N4, N5, and N6 may be any nucleotide in the above-described formula. Combinations of at least one (preferably one) of N1 and N2, N2 and N3, N3 and N4, N4 and N5, and N5 and N6 may be a two base CpG motif. When the four base CpG motif is not positioned between N3 and N4, any two contiguous bases in the middle 4 bases (4th to 7th bases) in the above-described formula may be a CpG motif and the other two bases may be any nucleotide. Further, a part of or the entire phosphodiester bond of an oligodeoxynucleotide may be substituted with a phosphorothioate bond. Preferably, the entire phosphodiester bond of an oligodeoxynucleotide is substituted with a phosphorothioate bond.

Type K CpG ODN suitably used in the present invention contains a non-palindromic structure comprising one or more CpG motifs. Type K CpG ODN more suit ably used in the present invention consists of a non-palindromic structure comprising 1 or more CpG motifs.

Type K CpG ODN contained in the oligodeoxynucleotide of the invention is preferably humanized. "Humanized" refers to having agonistic activity against human TLR9. Thus, the oligodeoxynucleotide of the invention comprising humanized type K CpG ODN has immunostimulatory activity unique to type K CpG ODN against humans (e.g., activity to activate human B cells to produce IL-6).

Humanized type K CpG ODN is generally characterized by a four base CpG motif consisting of TCGA or TCGT. In many cases, a single humanized type K CpG ODN comprises 2 or 3 of the four base CpG motifs. Thus, in a preferred embodiment, type K CpG ODN contained in the oligodeoxynucleotide of the invention comprises at least 1, more preferably 2 or more, and still more preferably 2 or 3 four base CpG motifs consisting of TCGA or TCGT. When such type K CpG ODN has 2 or 3 four base CpG motifs, these four base CpG motifs may be the same or different. However, this is not particularly limited, as long as there is agonist activity against human TLR9.

Type K CpG ODN included in the oligodeoxynucleotide of the invention more preferably comprises the nucleotide sequence set forth in the sequence (atcgactctc gagcgttctc (SEQ ID NO: 1)).

The length of type K CpG ODN is not particularly limited, as long as the oligodeoxynucleotide of the invention activates immunostimulatory activity (e.g., activity to activate B cells (preferably human B cells) to produce IL-6) or has anticancer activity, but the length is preferably 100 nucleotides long or less (e.g., 10 to 75 nucleotides long). The length of type K CpG ODN is more preferably 50 nucleotides long or less (e.g., 10 to 40 nucleotides long). The length of type K CpG ODN is still more preferably 30 nucleotides long or less (e.g., 10 to 25 nucleotides long). The length of type K CpG ODN is most preferably 12 to 25 nucleotides long.

As used herein, a "ligand" and "agonist" are interchangeably used, referring to a substance that expresses or enhances biological action of a receptor for a target entity (e.g., receptor). Examples thereof include naturally-occurring agonists (also referred to as ligands), synthetic agonists, altered agonists, and the like.

"STING" ((adapter molecule) stimulator of interferon genes)) identified as a membrane protein localized in the endoplasmic reticulum plays an important role in the biological defense mechanism against infections of various RNA viruses and DNA viruses. It is also reported that STING plays an important role in inducing natural immune responses against DNA components derived from microbes and viruses, but the molecular mechanism thereof had not been elucidated. In the present invention, the inventors elucidated that STING can form a complex with not only genomic DNA derived from viruses, but also synthetic double stranded DNA of 45 to 90 base pairs called ISD and self-DNA components derived from apoptotic cells. Analysis of DNA interaction region in vitro demonstrated that the C-terminus side region of STING is important. Recognition of various DNA components by STING was demonstrated to induce dynamic local change to regions surrounding the nuclear membrane of STING and to induce interferon production via activation of TBK1. It is also suggested that STING is possibly involved in the regulation of chronic inflammatory responses via recognition of not only allo-DNA component from a microorganism, but also auto-DNA component.

As used herein, a "STING ligand" and "STING agonist" are interchangeably used, which is a ligand (agonist) of "STING" ((adapter molecule) stimulator of interferon genes)) inducing type I IFN production and NF-κB mediated cytokine production. STING agonists are considered to be membrane proteins localized in the endoplasmic reticulum. As STING agonists, in addition to cGAMP, cyclic dinucleotides of microbial origin, c-di-AMP and c-di-GMP, are ligands of adapter molecule stimulators of IFN genes (STING), which signal through the TBK1-IRF3 axis to induce type I IFN production and NF-κB mediated cytokine production [Burdette et al., Nature. (2011) 478: 515-8; Mcwhirter et al., J. Exp. Med. (2009) 206: 1899-1911].

Recent studies report that these cyclic dinucleotides function as a potent vaccine adjuvant due to their ability to enhance antigen-specific T cells and humoral immune responses. Despite the above, the inventors' group has previously found that a STING agonist, DMXAA, unexpectedly induces a type 2 immune response via STING-IRF3 mediated type I IFN production [Tang et al., PLoS One. (2013) 8: 1-6]. Since type 2 immune responses cannot induce a type 1 immune response, the clinical usefulness of STING agonists, including cyclic dinucleotides, was debatable. For instance, the most common adjuvant, aluminum salt (alum), lacks the ability to induce cell-mediated immunity, which is understood to protect against cancer or diseases from intracellular pathogens [Hogenesch et al., Front. Immunol. (2013) 3: 1-13]. To overcome this limitation, alums were combined with many different types of adjuvants including monophosphoryl lipid A [Macleod et al., Proc. Natl. Acad. Sci. U.S.A (2011) 108: 7914-7919] and CpG ODN [Weeratna et al., Vaccine. (2000) 18: 1755-1762]. In regard to the techniques related to STING, especially when host DNA is unsuitably present in cytosol, host DNA may also be a sign of danger as in microorganism DNA, which results in interferon and inflammatory cytokine production [Desmet et al., Nat. Rev. Immunol. (2012) 12: 479-491; Barber et al., Immunol. Rev. (2011) 243: 99-108]. A recently identified cytosol DNA sensor is a cyclic GMP-AMP synthase (cGAS), which catalyzes the production of nonstandard cyclic dinucleotide cGAMP (2'3'-cGAMP) and contains a nonstandard 2',5' bond and 3',5' bond with the purine nucleoside thereof [Sun et al., Science. (2013) 339: 786-91]. Standard cGAMP (3'3') is synthesized in a microbe and has more variety of bonds than mammalian 2'3'-cGAMP. GMP and AMP nucleosides bind by a bis-(3',5') bond [Wu et al., Science. (2013) 339: 826-30; Zhang et al., Mol. Cell. (2013) 51: 226-35].

Thus, examples of STING agonists that can be used in the present invention include cyclic dinucleotides (CDN) such as 2'3'-cGAMP, c-di-AMP, 3'3'-cGAMP, and 3'2'-cGAMP, xanthenone derivatives such as DMXAA, and the like. STING agonists are also explained in WO 2010/017248, whose entire content is incorporated herein by reference.

As used herein, an "adjuvant" refers to an immunopotentiator that is added to increase the effect of a vaccine, which is an agent that is not a constituent of a specific antigen but increases immune responses to the administered antigen. With the recent development in immunology, the action mechanism of adjuvants ha's been gradually elucidated. Recently, various immunoregulatory properties of adjuvants are expected to be applied in prevention or therapy of not only infections, but also allergies, cancer, and autoimmune diseases.

Many vaccine adjuvants have been developed, mainly to induce antibody production (humoral immunity) up to this point. Many of the current adjuvants, including alum adjuvants, are thus humoral immunity inducing adjuvants called Th2 adjuvants. However, induction of cell-mediated immunity is more important than humoral immunity in the prevention or therapy of cancer or allergies. Such adjuvants are called Th1 adjuvants or type I adjuvants.

While many candidate substances of Th1 adjuvants have been reported, CpG oligonucleotide (CpG ODN) is considered the most effective. CpG ODN is demonstrated to be effective as a vaccine adjuvant of cancer or infection (Non Patent Literatures 1), but currently a more effective CpG ODN is being developed/improved (Non Patent Literature 2). If an effective and improved CpG ODN can be developed, this is more likely to be applied to therapy of cancer or allergy more than ever.

As used herein, a "type I adjuvant" is also called a Th1 adjuvant and refers to an adjuvant inducing a type I immune response. A type I adjuvant is typically characterized by an antitumor effect by natural killer cells or cytotoxic T cells.

As used herein, "type II adjuvant" is also called a Th2 adjuvant and refers to an adjuvant inducing a type II immune response. A type II adjuvant is typically characterized by the effect of preventing infections by inducing an antibody.

As used herein, "type I immune response" is also referred to as cell-mediated immunity, which is an immune system in which phagocytes, cytotoxic T cells (CTL; Cytotoxic T Lymphocytes), and natural killer cells are responsible for removing foreign substances in the body. T cells are associated therewith. Helper T cells include Th1 cells and Th2 cells, which are understood as suppressing each other's function by releasing a cytokine. These cells originally differentiated from a single cell called naïve T cell (Th0). Please refer to the section of T cells for the specific differentiation mechanism. Cells that have differentiated into Th1 cells from Th0 cells produce a so-called Th1 cytokine, such as IL-2, to activate CTL for destroying cells infected with a virus or the like. Cell-mediated immunity is involved not only in the removal of cells infected with a virus, but also with tumor immunity and transplantation immunity.

As used herein, a "type II immune response" is also referred to as humoral immunity and is an immune system centered around antibodies and complements. This is called as such because antibodies are dissolved in the serum. Macrophages, dendritic cells, and the like incorporate antigens into the cells and then dissolved the antigens and present a fragment thereof on a cell surface to function as antigen presenting cells. Antigen presenting cells present an antigen fragment via an MHC class II molecule and transmit a signal to a T cell antigen receptor (TCR; T Cell Receptor) on the naïve T cell (Th0) cell surface. The ratio of Th0 cells differentiating into type 1 helper T cells (Th1) and type 2 helper T cells (Th2) varies depending on the disease. In the presence of interleukin (IL)-4, IL-5, or the like called Th2 cytokines, Th0 differentiates into Th2 and induces humoral immunity.

As used herein, "immunoglobulin E" or "IgE" is a type of immunoglobulin and a glycoprotein that is present only in mammals. An IgE molecule is comprised of two heavy chains (e chain) and two light chains (κ chain and λ chain), and has two antigen binding sites. The IgE concentration in the serum of healthy individuals is in the unit of ng/ml and is significantly lower compared to other types of immunoglobulin. The concentration in the serum of a patient with an allergic disease increases, inducing a rapid release (degranulation reaction) of bioactive substances stored in mast cells or intracellular organelle of basophils. In view of the above, IgE is considered to be one of the molecules that plays a central role in allergic reactions, along with histamine.

As used herein, "allergy" refers to excessive immune responses to a specific antigen. Antigens from the environment causing allergies are especially called allergens. An "allergic disease" refers to a disease induced by an immune response to an exogenous antigen. However, this antigen is often harmless in a quantity that a patient is exposed to in normal life (e.g., pollen during spring time does not have toxicity in and of itself). An immune response resulting in unnecessary discomfort is experienced therewith. This is also called an allergic disease. Examples of typical diseases include atopic dermatitis, allergic rhinitis (hay fever), allergic conjunctivitis, allergic gastroenteritis, bronchial asthma, childhood asthma, food allergy, drug allergy, and hives. Recently, pathological conditions exhibiting a type 1 allergy symptom such as asthma or facial flash only from the scent of citrus or fragrance of gum or the like has drawn attention.

Meanwhile, "autoimmune disease" is a disease involving an immune response to a constituent substance of the patient's own body as an antigen. Autoimmune diseases may lead to a disorder or inflammation of a specific organ or site or a systemic symptom. Typical examples of such diseases include connective tissue diseases such as rheumatoid arthritis and alopecia areata.

As used herein, "interferon (IFN)" is a protein (cytokine) secreted by cells in response to infiltration of foreign substances such as pathogens (especially viruses) or tumor cells in the body of an animal. IFN-γ thereamong is a Th1 cytokine.

As used herein, "subject" refers to a target subjected to diagnosis, detection, therapy, or the like of the present invention (e.g., organism such as a human, or cells, blood, serum or the like extracted from an organism).

As used herein, "agent" is broadly used interchangeably and may be any substance or other element (e.g., light, radiation, heat, electricity, and other forms of energy) as long as the intended objective can be achieved. Examples of such a substance include, but are not limited to, proteins, polypeptides, oligopeptides, peptides, polynucleotides, oligonucleotides, nucleotides, nucleic acids (including for example DNAs such as cDNAs and genomic DNAs and RNAs such as mRNAs), polysaccharides, oligosaccharides, lipids, organic small molecules (e.g., hormones, ligands, information transmitting substances, organic small molecules, molecules synthesized by combinatorial chemistry, small molecules that can be used as medicine (e.g. small molecule ligands and the like) and a composite molecules thereof. Typical examples of an agent specific to a polynucleotide include, but are not limited to, polynucleotides with complementarity to a certain sequence homology (e.g., 70% or greater sequence identity) to a sequence of the polynucleotide, polypeptides such as transcription factors that bind to a promoter region, and the like. Typical examples of an agent specific to a polypeptide include, but are not limited to, antibodies directed specifically to the polypeptide or a derivative or analog thereof (e.g., single chain antibody), specific ligands or receptors when the polypeptide is a receptor or ligand, substrates when the polypeptide is an enzyme, and the like.

As used herein, "therapy" refers to the prevention of exacerbation, preferably maintaining the current condition, more preferably alleviation, and still more preferably elimination of a disease or disorder (e.g., cancer or allergy) in case of such a condition, including being capable of exerting a prophylactic effect or an effect of improving a disease in a patient, or of improving one or more symptoms accompanying the disease. Preliminary diagnosis conducted for suitable therapy may be referred to as a "companion therapy", and a diagnostic agent therefor may be referred to as "companion diagnostic agent".

As used herein, "therapeutic agent" broadly refers to all agents that are capable of treating a condition of interest (e.g., diseases such as cancer or allergy). In one embodiment of the present invention, "therapeutic agent" may be a pharmaceutical composition comprising an effective ingredient, and one or more pharmacologically acceptable carriers. A pharmaceutical composition can be manufactured, for example, by mixing an effective ingredient and the above-described carriers by any method known in the technical field of pharmaceuticals. Further, usage form of a therapeutic agent is not limited, as long as it is used for therapy. A therapeutic agent may consist solely of an effective ingredient or may be a mixture of an effective ingredient and any ingredient. Further, the shape of the above-described carriers is not particularly limited. For example, the carrier may be a solid or liquid (e.g., buffer). Therapeutic agents for cancer or allergies include drugs (prophylactic agent) used for the prevention of cancer, allergies, or the like, and suppressants of cancer, allergies, or the like.

As used herein, "prevention" refers to the act of taking a measure against a disease or disorder (e.g., allergy) from being in a condition, prior to the onset of such a condition. For example, it is possible to use the agent of the invention to perform diagnosis, and use the agent of the invention, as needed, to prevent or take measures to prevent allergies or the like.

As used herein, "prophylactic agent" broadly refers to all agents that are capable of preventing a condition of interest (e.g., disease such as allergy or the like).

As used herein, "kit" refers to a unit providing portions to be provided (e.g., testing agent, diagnostic agent, therapeutic agent, antibody, label, manual, and the like), generally in two or more separate sections. This form of a kit is preferred when a composition that should not be provided in a mixed state is preferably mixed immediately before use for safety reasons, or the like, is intended to be provided. Such a kit advantageously comprises instruction or manual preferably describing how the provided portions (e.g., testing agent, diagnostic agent, or therapeutic agent) should be used or how a reagent should be handled. When the kit is used herein as a reagent kit, the kit generally comprises an instruction describing how to use a testing agent, diagnostic agent, therapeutic agent, antibody, and the like.

As used herein, "instruction" is a document with an explanation of the method of use of the present invention for a physician or for other users. The instruction describes a detection method of the present invention, how to use a diagnostic agent, or a description instructing administration of a medicament or the like. Further, an instruction may have a description instructing oral administration, or administration to the esophagus (e.g., by injection or the like) as the site of administration. The instruction is prepared in accordance with a format defined by a regulatory authority of the country in which the present invention is practiced (e.g., Health, Labor and Welfare Ministry in Japan, Food and Drug Administration (FDA) in the U.S. or the like), with an explicit description showing approval by the regulatory authority. The instruction is a so-called package insert and is generally provided in, but not limited to, paper media. The instructions may also be provided in a form such as electronic media (e.g., web sites provided on the Internet or emails).

(Preferred Embodiments)

The preferred embodiments of the present invention are explained hereinafter. It is understood that the embodiments provided hereinafter are provided to better facilitate the understanding of the present invention, and the scope of the present invention should not be limited by the following description. Thus, it is apparent that those skilled in the art can refer to the descriptions herein to appropriately make modifications within the scope of the present invention. It is also understood that the following embodiments of the present invention can be used individually or as a combination.

<Combination of CpG and STING Agonist>

In one aspect, the present invention provides a combination of a CpG oligonucleotide and a STING agonist (also referred to as a STING ligand). The combination of the invention can be used for various therapies or for prevention, such as therapy or prevention of cancer, allergies or the like, or for therapy or prevention utilizing immunostimulation.

Thus, the present invention provides a method of treating or preventing a disease, comprising administering an effective amount of a combination of a CpG oligonucleotide and a STING agonist to a subject in need thereof.

In one embodiment, the combination of the invention is for use as a type I adjuvant. This phenomenon is unexpected from the viewpoint of both aspects. That is, from the viewpoint of the STING agonist, this ligand is generally considered to only exert humoral immunity, i.e., an infection preventing effect through antibody induction, but cell-mediated immunity is elicited by adding CpG. Such a "switch" effect is truly unexpected. Further, the effect of eliciting cell-mediated immunity of CpG was significantly enhanced with a STING agonist. Considering that a STING agonist has hardly any effect on eliciting cell-mediated immunity, a significant enhancement that was quantitatively unexpected is exhibited, even after considering the effect of eliciting the cell-mediated immunity of CpG.

In another embodiment, the combination of the invention is for suppressing IgE inducing action of the STING agonist. Although not wishing to be bound by any theory, it was unexpectedly discovered for the first time by the present invention that a STING agonist has IgE inducing action which may lead to an allergic side effect. While such a problem needs to be addressed, it was unexpected that this was solved by CpG.

In one embodiment, examples of the STING agonist include 3'3'-cGAMP, 2'3'-cGAMP, 2'2'-cGAMP, DMXAA, c-di-AMP, c-di-GMP, and the like. DMXAA is a mouse specific STING agonist which is understood as having little effect in humans. 3'3'-cGAMP is a microbial cGMAP. 2' 3'-cGAMP is a mammalian cGAMP, and 2' 2'-cGAMP is non-naturally occurring cGAMP.

In one embodiment, the CpG oligonucleotide of the invention is a type K/B oligonucleotide. Although not wishing to be bound by any theory, this is because a type K/B oligonucleotide, especially CpG ODN, is demonstrated to be effective as a vaccine adjuvant for cancer or infection, while this can be further enhanced by the present invention.

In one embodiment, CpG oligonucleotides that can be used in the present invention can be any common CpG, including, but not limited to, K3 CpG (SEQ ID NO: 1=5'-atcgactatcgagagttctc-3'), CpG 1826 (SEQ ID NO: 2=5'-tccatgacgttcctgacgtt-3'), D35 CpG (SEQ ID NO: 3=5'-ggtg-catcgatgcagggggg-3'), and the like.

In one embodiment, examples of STING agonists that can be used in the present invention include cGAMP, 3'3'-cGAMP, c-di-AMP, c-di-GAMP, 2'3'-cGAMP, DMXAA, and the like.

In one specific embodiment, the combination of the invention is used as an anticancer agent. In this case, the method of treating or preventing of the present invention is provided as a method of treating or preventing cancer.

In one embodiment, the anticancer agent can be targeted for cancer such as lymphoma or melanoma.

In another embodiment, the combination of the invention reduces or eliminates a type II immune response and/or expresses or enhances a type I immune response.

In another embodiment, the combination of the invention is for inducing interferon γ (IFN-γ). Alternatively, the combination of the invention is for use as a vaccine adjuvant. In this case, the method of treating or preventing of the invention is provided as a method of inactivating immunity.

These two agents (CpG oligonucleotide and STING agonist) may be administered concomitantly, at different times, as part of the same formulation, as a combination of different formulations, in order, or separately.

T cell activation can be assayed, for example, as follows. In some embodiments, various assays can be utilized to determine whether an immune response is stimulated in a T cell or a group of T cells (i.e., whether a T cell or a group of T cells are "activated"). In some embodiments, stimulation of an immune response in T cells can be determined by measuring the antigen induced production of cytokines by the T cells. In some embodiments, stimulation of an immune response in T cells can be determined by measuring the antigen induced production of IFNγ, IL-4, IL-2, IL-10, IL-17, and/or TNFα by the T cells. In some embodiments, antigen generating production of cytokines by T cells can be measured by flow cytometry after cytokine staining in the cells. In some embodiments, the antigen induced production of cytokines by T cells can be measured by flow cytometry after surface trapping staining. In some embodiments, antigen induced production of cytokines by T cells can be determined by measuring the cytokine concentration in the supernatant of activated T cell culture. In some embodiments, this can be measured by ELISA.

In some embodiments, antigen generating production of cytokines by T cells can be measured by an ELISPOT assay. In general, ELISPOT assays use an approach that is very similar to the approach of a sandwich enzyme-linked immunosorbent assay (ELISA). Antibodies (e.g., monoclonal antibodies, polyclonal antibodies, and the like) are aseptically coated on a PVDF (polyvinylidene fluoride)—backed microplate. Antibodies are selected for specificity to a target cytokine. The plate is blocked (e.g., by using a serum protein that is not reactive to any of the antibodies in the assay). The cells of interest are plated at various densities with an antigen or mitogen, and then are left standing over a designated period of time in a humidified 37° C. $Co_2$ incubator. Cytokines secreted by activated cells are locally trapped by antibodies coated on a PVDF film with a wide surface area. The wells are washed to remove cells, debris, and culture components, and then a secondary antibody specific to the cytokine (e.g., biotinylated polyclonal antibody) is added to the wells. This antibody is reactive to different epitopes of a target cytokine. Thus, trapped cytokines are detected by the use thereof. After removing any unbound biotinylated antibodies by washing, detected cytokines are made visible using avidin-HRP and a promoting substrate (e.g., AEC or BCIP/NBT). Colored final products (spots, generally dark blue) typically represent individual cytokine producing cells. The spots can be counted manually (e.g., using a dissecting microscope) or by using an automatic reader for capturing images of microwells to analyze the number and size of the spots. In some embodiments, each spot corresponds to a single cytokine producing cell.

In some embodiments, immune responses in T cells are considered stimulated when about 1% to about 100% of antigen specific T cells are producing cytokines. In some embodiments, immune responses in T cells are considered stimulated when at least about 1%, at least about 5%, at least about 10%, at least about 25%, at least about 50%, at least about 75%, at least about 90%, at least about 95%, at least about 99%, or about 100% of antigen specific T cells are producing cytokines.

In some embodiments, immune responses in T cells are considered stimulated when an immunized subject comprise at least about 10-fold, at least about 50-fold, at least about 100-fold, at least about 500-fold, at least about 1000-fold, at least about 5000-fold, at least about 10,000-fold, at least about 50,000-fold, at least about 100,000-fold, or at least greater than about 100,000-fold more cytokine producing cells than an untreated control.

In some embodiments, stimulation of immune responses in T cells can be determined by measuring the antigen induced growth of the T cells. In some embodiments, the antigen induced growth can be measured as $H^3$-thymidine intake in divided T cells (also called "lymphocyte transformation test" or "LTT" in some cases). In some embodiments, antigen induced growth is recognized when $H^3$-thymidine intake (give as a count from a γ counter) is at least about 5-fold, at least about 10-fold, at least about 20-fold, at least about 50-fold, at least about 100-fold, at least about 500-fold, at least about 1000-fold, at least about 5000-fold, at least about 10,000-fold, or at least greater than about 10,000-fold higher than that of an untreated control.

In some embodiments, antigen induced growth can be measured by flow cytometry. In some embodiments, antigen induced growth can be measured by a carboxyfluorescein succinimidyl ester (CFSE) dilution assay. CFSE is a non-toxic, fluorescent, membrane-permeable pigment that binds to an amino group of a cytosolic protein (e.g., T cell protein) by a succinimidyl reactive group thereof. When cells divide, CFSE labeled proteins are equally distributed to daughter cells. Thus, cell fluorescence is reduced by half by each division. As a result, antigen specific T cells will lose their fluorescence after being cultured in the presence of corresponding antigens ($CFSE^{low}$) such that they are distinguishable from other cells ($CFSE^{high}$) in the culture. In some embodiments, antigen inducing growth is recognized when the CFSE dilution (given as a percentage of $CFSE^{low}$ cells to all $CFSE^+$ cells) is at least about 5%, at least about 10%, at least about 25%, at least about 50%, at least about 75%, at least about 90%, at least about 95%, or at least about 100%.

In some embodiments, immune responses in T cells are considered stimulated when a cell marker of T cell activation is expressed at a different level (e.g., higher or lower level) than the level in unstimulated cells. In some embodiments, CD11aCD27, CD25, CD40L, CD44, CD45RO and/or CD69 are expressed at a higher level in activated T cells compared to unstimulated T cells. In some embodiments L-selectin (CD62L), CD45RA, and/or CCR7 are not expressed at such a high level in activated T cells compared to unstimulated T cells.

In some embodiments, immune responses in T cells are measured by assaying cytotoxicity of effector $CD8^+$ T cells to antigen-pulsed target cells. For example, $^{51}$chromium ($^{51}$Cr) release assay can be performed. In this assay, effector $CD8^+$ T cells bind to infected cells presenting a viral peptide on class IMHC, to signal apoptosis of the infected cells. When the cells are labeled with $^{51}$Cr before the effector $CD8^+$ T cells are added, the amount of $^{51}$Cr released into the supernatant is proportional to the number of killed targets.

Those skilled in the art understand that the aforementioned assay is merely an exemplary method that can be used to determine whether T cells are activated. Any assay known to those skilled in the art that can be used to determine whether T cells are activated is encompassed in the scope of the present invention. The assay used in the present invention and additional assays that can be used to determine whether T cells are activated are described in Current Protocols in Immunology (John Wiley & Sons, Hoboken, N.Y., 2007; incorporated herein by reference).

<Application of STING Agonist Itself as Type I Adjuvant Formulation>

In another aspect, the present invention provides a composition for use as a type I adjuvant, comprising a STING agonist, wherein the STING agonist is administered with a CpG oligonucleotide. It is understood that one or more of the STING agonists and CpG oligonucleotides used herein in any form described elsewhere herein, including <Combination of CpG and STING agonist> and Examples, can be combined for use.

Thus, the present invention is a method for treating or preventing a disease in a subject, comprising administering a composition for use as a type I adjuvant, wherein the composition comprises an effective amount of STING agonist to a subject in need thereof, wherein the STING agonist is administered with a CpG oligonucleotide. In this case, the CpG oligonucleotide can be administered simultaneously with, before, or after the administration of the STING agonist. Thus, the present invention provides a method for exerting a type I adjuvant effect of a STING agonist, comprising administering the STING agonist with a CpG oligonucleotide.

In one embodiment, examples of diseases that can be treated or prevented by the present invention utilizing an adjuvant enhancing effect include cancer, allergies, virus or microbial infections, and the like. More specifically, diseases that can be treated or prevented by the present invention utilizing an adjuvant enhancing effect are cancer. Examples of such cancer include lymphoma, melanoma, and the like.

These two agents (CpG oligonucleotide and STING agonist) may be administered concomitantly, at different times, as part of the same formulation, as a combination of different formulations, in order, or separately.

<Type I Adjuvant Formulation Enhancing Effect of STING Agonist on CpG>

In another aspect, the present invention provides an action enhancing agent for a type I adjuvant of a CpG oligonucleotide, comprising a STING agonist. It is understood that one or more of the STING agonists and CpG oligonucleotides used herein in any form described elsewhere herein, including <Combination of CpG and STING agonist> and Examples, can be combined for use.

Thus, the present invention provides a method of enhancing action of a type I adjuvant of a CpG oligonucleotide, comprising administering a composition comprising an effective amount of a STING agonist to a subject. Thus, the present invention also provides a method of enhancing action of a type I adjuvant of a CpG oligonucleotide, comprising administering the CpG oligonucleotide with a STING agonist.

These two agents (CpG oligonucleotide and STING agonist) may be administered concomitantly, at different times, as part of the same formulation, as a combination of different formulations, in order, or separately.

<Use of STING Agonist as Anticancer Agent>

In another aspect, the present invention provides an anticancer agent comprising a STING agonist, wherein the STING agonist is administered with a CpG oligonucleotide. It is understood that one or more of the STING agonists and CpG oligonucleotides used herein in any form described elsewhere herein, including <Combination of CpG and STING agonist> and Examples, can be combined for use.

Thus, the present invention provides a method of treating or preventing cancer in a subject, comprising administering an effective amount of an anticancer agent comprising a STING agonist to the subject, wherein the STING agonist is administered with a CpG oligonucleotide. Thus, the present invention provides a method of treating or preventing cancer, wherein the method comprises administering an anticancer agent comprising a STING agonist with a CpG oligonucleotide.

In one embodiment, target cancer that can be treated or prevented with the present invention utilizing a STING agonist includes lymphoma, melanoma, and the like.

These two agents (CpG oligonucleotide and STING agonist) may be administered concomitantly, at different times, as part of the same formulation, as a combination of different formulations, in order, or separately.

<Use of CpG Oligonucleotide as Anticancer Agent>

In another aspect, the present invention provides an anticancer agent comprising a CpG oligonucleotide, wherein the CpG oligonucleotide is administered with a STING agonist. It is understood that one or more of the STING agonists and CpG oligonucleotides used herein in any form described elsewhere herein, including <Combination of CpG and STING agonist> and Examples, can be combined for use.

Thus, the present invention provides a method of treating or preventing cancer, comprising administering an effective amount of an anticancer agent comprising a CpG oligonucleotide to a subject, wherein the CpG oligonucleotide is administered with a STING agonist. Thus, the prevent invention provides a method of treating or preventing cancer, wherein the method comprises administering an anticancer agent comprising a CpG oligonucleotide with a STING agonist.

In one embodiment, examples of cancer that can be treated or prevented with the present invention utilizing a CpG oligonucleotide include, but are not limited to, lymphoma, melanoma, and the like.

These two agents (CpG oligonucleotide and STING agonist) may be administered concomitantly, at different times, as part of the same formulation, as a combination of different formulations, in order, or separately.

<Suppression of Allergy (IgE) Inducing Action of STING Agonist by CpG>

In another aspect, the present invention provides a composition for reducing or eliminating IgE inducing action of a STING agonist, comprising a CpG oligonucleotide. It is understood that one or more of the STING agonists and CpG oligonucleotides used herein in any form described elsewhere herein, including <Combination of CpG and STING agonist> and Examples, can be combined for use.

Thus, the present invention provides a method of reducing or eliminating IgE inducing action of a STING agonist, comprising administering a composition comprising an effective amount of a CpG oligonucleotide to a subject. Thus, the present invention provides a method of reducing or eliminating IgE inducing action of a STING agonist, wherein the method comprises administering a CpG oligonucleotide when using the STING agonist.

In one embodiment, examples of allergies that can be treated or prevented by the present invention include, but are not limited to, allergies that are side effects of a STING agonist, as well as atopic dermatitis, allergic rhinitis (hay fever), allergic conjunctivitis, allergic gastroenteritis, bronchial asthma, childhood asthma, food allergy, drug allergy, hive, and the like.

These two agents (CpG oligonucleotide and STING agonist) may be administered concomitantly, at different times, as part of the same formulation, as a combination of different formulations, in order, or separately.

In one embodiment, allergy inducting action of the STING agonist is reduced or eliminated.

(Medicaments, Dosage Forms, Etc.)

The present invention is provided as medicaments (therapeutic agent or prophylactic agent) in various forms described above.

The route of administration of a therapeutic agent, prophylactic agent, or the like that is effective upon therapy is preferably used, such as intravenous, subcutaneous, intramuscular, intraperitoneal, oral administration, or the like. Examples of dosage form include injection, capsules, tablets, granules, and the like. The components of the present invention are effectively used upon administration as an injection. Aqueous solutions for injection may be stored, for example, in a vial or a stainless steel container. Aqueous solutions for injections may also be blended with, for example, saline, sugar (e.g., trehalose), NaCl, NaOH, or the like. Therapeutic agents may also be blended, for example, with a buffer (e.g., phosphate buffer), stabilizer, or the like.

In general, the composition, medicament, therapeutic agent, prophylactic agent, or the like of the present invention comprises a therapeutically effective amount of a therapeutic agent or effective ingredient, and a pharmaceutically acceptable carrier or excipient. As used herein, "pharmaceutically acceptable" means that a substance is approved by a government regulatory agency or listed in the pharmacopoeia or other commonly recognized pharmacopoeia for use in animals, more specifically in humans. As used herein "carrier" refers to a diluent, adjuvant, excipient or vehicle administered with a therapeutic agent. Such a carrier can be an aseptic liquid such as water or oil, including, but not limited to, those derived from petroleum, animal, plant or synthesis, as well as peanut oil, soybean oil, mineral oil, sesame oil, and the like. When a medicament is orally administered, water is a preferred carrier. For intravenous administration of a pharmaceutical composition, saline and aqueous dextrose are preferred carriers. Preferably, an aqueous saline solution and aqueous dextrose and glycerol solution are used as a liquid carrier of an injectable solution. Suitable excipients include light anhydrous silicic acid, crystalline cellulose, mannitol, starch, glucose, lactose, sucrose, gelatin, malt, rice, wheat flour, chalk, silica gel, sodium stearate, glyceryl monostearate, talc, sodium chloride, powdered skim milk, glycerol, propylene, glycol, water, ethanol, carmellose calcium, carmellose sodium, hydroxypropyl cellulose, hydroxypropyl methylcellulose, polyvinyl acetal diethylamino acetate, polyvinylpyrrolidone, gelatin, medium-chain fatty acid triglyceride, polyoxyethylene hydrogenated castor oil 60, saccharose, carboxymethylcellulose, corn starch, inorganic salt, and the like. When desirable, the composition can also contain a small amount of wetting agent, emulsifier, or pH buffer. These compositions can be in a form of a solution, suspension, emulsion, tablet, pill, capsule, powder, sustained release preparation, or the like. It is also possible to use traditional binding agents and carriers, such as triglyceride, to prepare a composition as a suppository. Oral preparation can also comprise a standard carrier such as medicine grade mannitol, lactose, starch, magnesium stearate, sodium saccharin, cellulose, or magnesium carbonate. Examples of a suitable carrier are described in E. W. Martin, Remington's Pharmaceutical Sciences (Mark Publishing Company, Easton, U.S.A.). Such a composition contains a therapeutically effective amount of therapy agent, preferably in a purified form, together with a suitable amount of carrier, such that the composition is provided in a form suitable for administration to a patient. A preparation must be suitable for the administration format. In addition, the composition may comprise, for example, a surfactant, excipient, coloring agent, flavoring agent, preservative, stabilizer, buffer, suspension, isotonizing agent, binding agent, disintegrant, lubricant, fluidity improving agent, corrigent, or the like.

Examples of "salt" in one embodiment of the present invention include anionic salts formed with any acidic (e.g., carboxyl) group and cationic salts formed with any basic (e.g., amino) group. Salts include inorganic salts and organic salts, as well as salts described in, for example, Berge et al., J. Pharm. Sci., 1977, 66, 1-19. Examples thereof further include metal salts, ammonium salts, salts with organic base, salts with inorganic acid, salts with organic acid, and the like. "Solvate" in one embodiment of the present invention is a compound formed with a solute or solvent. For example, J Honig et al., The Van Nostrand Chemist's Dictionary P650 (1953) can be referred for solvates. When a solvent is water, a solvate formed thereof is a hydrate. It is preferable that the solvent does not obstruct the biological activity of the solute. Examples of such a preferred solvent include, but not particularly limited to, water and various buffers. Examples of "chemical modification" in one embodiment of the present invention include modifications with PEG or a derivative thereof, fluorescein modification, biotin modification, and the like.

When the present invention is administered as a medicament, various delivery systems are known, which can be used to administer the agent of the invention to a suitable site (e.g., esophagus). Examples of such a system include use of a recombinant cell that can express encapsulated therapeutic agent (e.g., polypeptide) in liposomes, microparticles, and microcapsules; use of endocytosis mediated by a receptor; construction of a therapy nucleic acid as a part of a retrovirus vector or another vector; and the like. Examples of the method of introduction include, but are not limited to, intradermal, intramuscular, intraperitoneal, intravenous, subcutaneous, intranasal, epidural, and oral routes. A medicament can be administered by any suitable route, such as by injection, bolus injection, or by absorption through epithelial or mucocutaneous lining (e.g., oral cavity, rectum, intestinal mucosa, or the like). In addition, an inhaler or mistifier using an aerosolizing agent can be used as needed. Moreover, other biological activating agents can also be administered concomitantly. Administration can be systemic or local. When the present invention is used for cancer, the present invention can be administered by any suitable route such as direct injection into cancer (lesion).

In a preferred embodiment, a composition can be prepared as a pharmaceutical composition adapted to administration to humans in accordance with a known method. Such a composition can be administered by an injection. A composition for injection is typically a solution in an aseptic isotonic aqueous buffer. A composition can also comprise a local anesthetic such as lidocaine, which alleviates the pain at the site of injection, and a solubilizing agent as needed. Generally, ingredients can be supplied individually or by mixing the ingredients together in a unit dosage form; and supplied, for example, in a sealed container such as an ampoule or sachet showing the amount of active agent or as a lyophilized powder or water-free concentrate. When a composition is to be administered by injection, the composition can be distributed using an injection bottle containing aseptic agent-grade water or saline. When composition is to be administered by injection, an aseptic water or saline ampoule for injection can also be provided such that the ingredients can be mixed prior to administration.

The composition, medicament, therapeutic agent, and prophylactic agent of the invention can be prepared as a neutral or base form or other prodrugs (e.g., ester or the like). Pharmaceutically acceptable salts include salts formed with a free carboxyl group, derived from hydrochloric acid, phosphoric acid, acetic acid, oxalic acid, tartaric acid, or the like, salts formed with a free amine group, derived from isopropylamine, triethylamine, 2-ethylaminoethanol, histidine, procaine, or the like; and salts derived from sodium, potassium, ammonium, calcium, ferric hydroxide or the like.

The amount of therapeutic agent of the invention that is effective in therapy of a specific disorder or condition may vary depending on the properties of the disorder or condition. However, such an amount can be determined by those skilled in the art with a standard clinical technique based on the descriptions herein. Furthermore, an in vitro assay can be used in some cases to assist the identification of the optimal dosing range. The precise dose to be used for a preparation may also vary depending on the route of administration or the severity of the disease or disorder. Thus, the dose should be determined in accordance with the judgment of the attending physician or the condition of each patient. The dosage is not particularly limited, but may be 0.001, 1, 5, 10, 15, 100, or 1000 mg/kg body weight per dosage or within a range between any two values described above. The dosing interval is not particularly limited, but may be, for example, 1 or 2 doses every 1, 7, 14, 21, or 28 days or 1 or 2 doses in a range of period between any two values described above. The dosage, dosing interval, and dosing method may be appropriately selected depending on the age, weight, symptom, target organ, or the like of the patient. Further, it is preferable that a therapeutic agent contains a therapeutically effective amount of effective ingredients, or an amount of effective ingredients effective for exerting a desired effect. When a malignant tumor marker significantly decreases after administration, the presence of a therapeutic effect may be acknowledged. The effective dose can be estimated from a dose-response curves obtained from in vitro or animal model testing systems.

"Patient" or "subject" in one embodiment of the present invention includes humans and mammals excluding humans (e.g., one or more species of mice, guinea pigs, hamsters, rats, rabbits, pigs, sheep, goats, cows, horses, cats, dogs, marmosets, monkeys, and the like).

The pharmaceutical composition, therapeutic agent, or prophylactic agent of the invention can be provided as a kit.

In a specific embodiment, the present invention provides an agent pack or kit comprising one or more containers filled with one or more ingredients of the composition or medicament of the invention. Optionally, information indicating approval for manufacture, use, or sale for administration to a human by a government agency regulating the manufacture, use, or sale of medicaments or biological products can be appended to such a container in a stipulated form.

In a specific embodiment, the pharmaceutical composition comprising an ingredient of the present invention can be administered via liposomes, microparticles, or microcapsules. In various embodiments of the present invention, it may be useful to use such a composition to achieve sustained release of the ingredient of the present invention.

The formulation procedure for the therapeutic agent, prophylactic agent, or the like of the invention as a medicament or the like is known in the art. The procedure is described, for example, in the Japanese Pharmacopoeia, the United States Pharmacopeia, pharmacopeia of other countries, or the like. Thus, those skilled in the art can determine the embodiment such as the amount to be used without undue experimentation from the descriptions herein.

(General Techniques)

Molecular biological approaches, biochemical approaches, and microbiological approaches used herein are well known and conventional approaches in the art that are described in, for example, Sambrook J. et al. (1989). Molecular Cloning: A Laboratory Manual, Cold Spring Harbor and its 3rd Ed. (2001); Ausubel, F. M. (1987). Current Protocols in Molecular Biology, Greene Pub. Associates and Wiley-Interscience; Ausubel, F. M. (1989). Short Protocols in Molecular Biology: A Compendium of Methods from Current Protocols in Molecular Biology, Greene Pub. Associates and Wiley-Interscience; Innis, M. A. (1990). PCR Protocols: A Guide to Methods and Applications, Academic Press; Ausubel, F. M. (1992). Short Protocols in Molecular Biology: A Compendium of Methods from Current Protocols in Molecular Biology, Greene Pub. Associates; Ausubel, F. M. (1995). Short Protocols in Molecular Biology: A Compendium of Methods from Current Protocols in Molecular Biology, Greene Pub. Associates; Innis, M. A. et al. (1995). PCR Strategies, Academic Press; Ausubel, F. M. (1999). Short Protocols in Molecular Biology: A Compendium of Methods from Current Protocols in Molecular. Biology, Wiley, and annual updates; Sninsky, J. J. et al. (1999). PCR Applications: Protocols for Functional Genomics, Academic Press, Bessatsu Jikken Igaku [Experimental Medicine, Supplemental Volume], Idenshi Donyu Oyobi Hatsugen Kaiseki Jikken Ho [Experimental Methods for Transgenesis & Expression Analysis], Yodosha, 1997 and the like. The relevant portions (which can be the entire document) of the above documents are incorporated herein by reference.

DNA synthesis techniques and nucleic acid chemistry for making an artificially synthesized gene are described in, for example, Gait, M. J. (1985). Oligonucleotide Synthesis: A Practical Approach, IRL Press; Gait, M. J. (1990). Oligonucleotide Synthesis: A Practical Approach, IRL Press; Eckstein, F. (1991). Oligonucleotides and Analogues: A Practical Approach, IRL Press; Adams, R. L. et al. (1992). The Biochemistry of the Nucleic Acids, Chapman & Hall; Shabarova, Z. et al. (1994). Advanced Organic Chemistry of Nucleic Acids, Weinheim; Blackburn, G. M. et al. (1996). Nucleic Acids in Chemistry and Biology, Oxford University Press; Hermanson, G. T. (1996). Bioconjugate Techniques, Academic Press and the like, the relevant portions of which are incorporated herein by reference.

For example, as used herein, the oligonucleotide of the invention can also be synthesized by a standard method known in the art, such as by using an automated DNA synthesizer (a synthesizer commercially available from Biosearch, Applied Biosystems or the like). For example, a phosphorothioate-oligonucleotide can also be synthesized by the method of Stein et al. (Stein et al., 1988, Nucl. Acids Res. 16: 3209), and a methyl phosphonate-oligonucleotide can also be prepared using a controlled pore glass polymer support (Sarin et al., 1988, Proc. Natl. Acad. Sci. USA 85: 7448-7451)

As used herein, "or" is used when "at least one or more" of the matters listed in the sentence can be employed. When explicitly described herein as "within the range of two values", the range also includes the two values themselves.

Reference literatures such as scientific literatures, patents, and patent applications cited herein are incorporated herein by reference to the same extent that the entirety of each document is specifically described.

As described above, the present invention has been described while showing preferred embodiments to facilitate understanding. The present invention is described hereinafter based on Examples. The aforementioned description and the following Examples are not provided to limit the present invention, but for the sole purpose of exemplification. Thus, the scope of the present invention is not limited to the embodiments and Examples specifically described herein and is limited only by the scope of claims.

EXAMPLES

The Examples are described hereinafter. When necessary, animals were handled in compliance with the standards set forth by the National Institute of Biomedical Innovation and/or the Osaka University, based on the Declaration of Helsinki. For reagents, the specific products described in the Examples were used. However, the reagents can be substituted with an equivalent product from another manufacturer (Sigma-Aldrich, Wako Pure Chemical, Nacalai Tesque, R & D Systems, USCN Life Science INC, or the like).

(General Approach)

(Materials and Methods)

(Mice)

7 to 10 week old female C57BL/6J mice were purchased from CLEA JAPAN INC. (Osaka, Japan). MyD88 KO mice were purchased from Oriental BioService Inc. (Kyoto, Japan). IL-12p40 KO and STING mutant mice (Tmem173gt) having a loss-of-function mutation at a ligand binding site of STING [Sauer et al., Infect. Immun. (2011) 79: 688-94] were purchased from Jackson Laboratories (Bar Harbor, Me., USA). IRF3/7 DKO mice were produced from IRF3 KO [Tang et al., PLoS One. (2013) 8: 1-6] and IRF7 KO mice, the latter of which were provided by RIKEN BRC (Ibaraki, Japan) through the National Bio-Resource Project of MEXT. IFNAR2 KO mice were obtained from B&K Universal. All animal experiments were conducted in accordance with the guidelines of the Animal Care and Use Committee of RIMD and Osaka University Immunology Frontier Research Center (IFReC). The use of animals was approved by the Osaka University.

(Reagents)

2'3'-cGAMP, c-di-GMP, and 3'3'-cGAMP were purchased from Invivogen (San Diego, Calif., USA), DMXAA was purchased from Sigma-Aldrich (St. Louis, Mo., USA) and was dissolved into 5% $NaHCO_3$. Yamasa (Chiba, Japan) provided c-di-GMP. OVA was purchased from Kanto Kagaku (Osaka, Japan), and the endotoxin level was determined to be less than 1 EU/mg with Toxicolor® (Seikagaku Corporation, Tokyo, Japan). K3 CpG ODN (SEQ ID NO: 1) was synthesized by Gene Design (Ibaraki, Osaka, Japan) as previously described.

(Cytokine Measurement)

Mouse IL-12p40, mouse IL-13, and human IFNγ levels were measured using an ELISA kit available from BioLegend (San Diego, Calif., USA).

(Statistical Analysis)

Mann-Whitney U test, Student's t-test, or one-way ANOVA including Bonferroni multiple comparison test was used for statistical analysis (*$p<0.05$; $p<0.01$; *$p<0.001$). Statistical analysis was performed using GraphPad Prism software (La Jolla, Calif., USA).

Example 1: Immunization and Culture of Splenocytes

After anesthesia, C57BL/6J mice were immunized intramuscularly on day 0 and day 10 with OVA (10 μg), OVA and K3 CpG (10 μg), DMXAA (50 μg), c-di-GMP (1 μg), 2'3'-cGAMP or 3'3'-cGAMP (1 μg), or K3 CpG+2'3'-cGAMP/3'3'-cGAMP/c-di-GMP/DMXAA. On day 17, OVA specific sera IgG1 and IgG2c were measured by ELISA as previously described [Kuroda et al., Immunity. (2011) 34; 514-526]. The secondary antibodies used in ELISA of IgG2c and IgG1 were horseradish peroxidase conjugate goat anti-mouse IgG2c and IgG1 (Bethyl Laboratories, Montgomery, Tex.). On day 17, splenocytes were collected to prepare a single cell suspension using gentle MACS dissociator (miltenyi Biotech, Gladbach, Germany). After dissolution of erythrocytes using a Tris-NH$_4$Cl buffer, fat was cultured in RPMI (containing 1% penicillin/streptomycin and 10% fetal calf serum (FCS)) and was stimulated for 48 hours with whole OVA (10 μg/ml) or MHC class I or MHC class II specific OVA peptide (OVA257 and OVA323, respectively) (10 μg/ml). IFNγ and IL-13 production was measured by ELISA.

(Results: Combination of TLR9-Agonist and STING-Agonist is Type 1 Adjuvant and Suppresses Type 2 Immune Response)

Figure 3A:
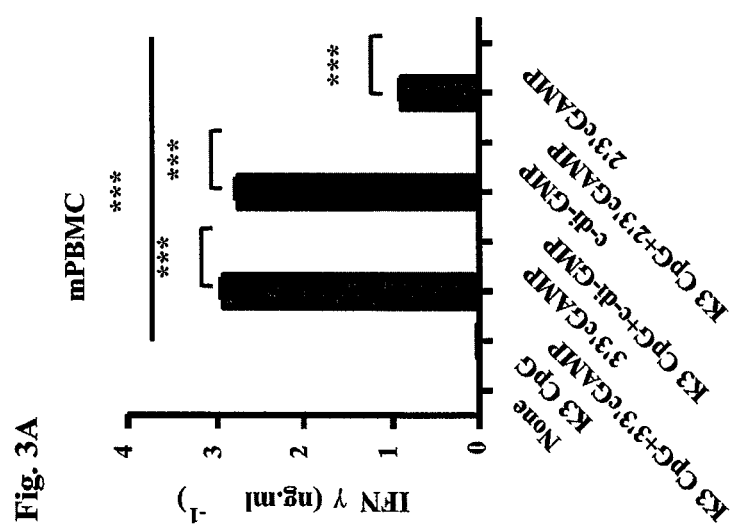
FIG. 3A shows the concentration of IFNγ produced in the supernatant of a mouse PBMC culture.

In view of the report that agonists such as STING agonists, DMXAA, c-di-GMP, and mammalian 2' 3'-cGAMP induce type 2 immune responses [Zhang et al., Mol. Cell. (2013) 51: 226-35; Burdette et al., Nature. (2011) 478: 515-8; Tang et al., PLoS One. (2013) 8: 1-6], the inventors have investigated the ability of K3 CpG to cooperate with these other STING agonists. Mouse PBMCs were not only stimulated with 3'3'-cGAMP, but also 2'3'-cGAMP and c-di-GMP in cooperation with K3 CpG to induce the production of congenital IFNγ (FIG. 3A).

Figure 3B:
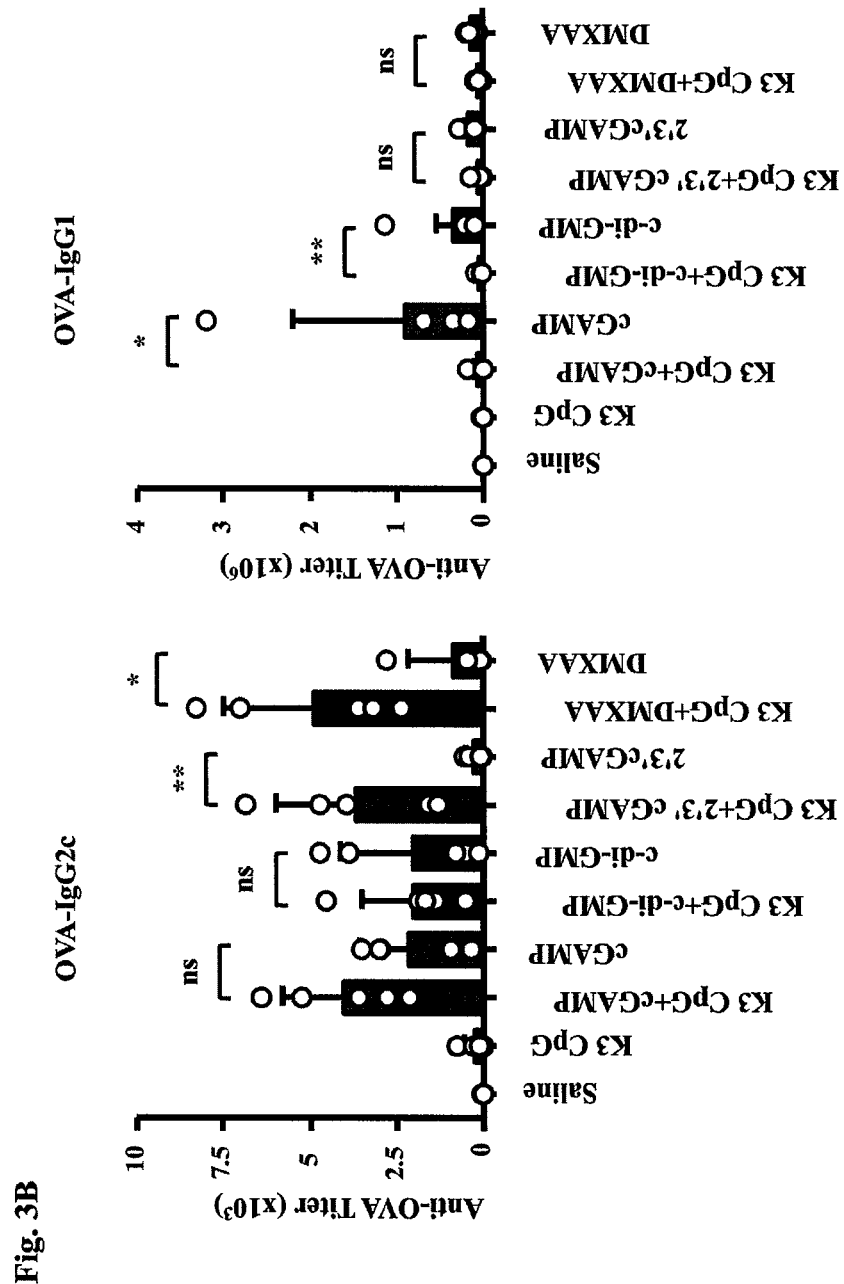
FIG. 3B shows the anti-OVA antibody titer of the serum in mice immunized with OVA. The left panel shows the anti-OVA antibody titer of IgG2c, and the right panel shows the anti-OVA antibody titer of IgG1. Each panel shows, from the left, saline, K3 CpG, K3 CpG+3'3'-cGAMP, 3'3'-cGAMP, K3 CpG+c-di-GMP, c-di-GMP, K3 CpG+2'3'-cGAMP, 2'3'-cGAMP, and DMXAA. A combination of a TLR9-agonist and a STING-agonist is a potent type 1 adjuvant that also suppresses type 2 immune responses in vivo. Mice were immunized intramuscularly on day 0 and day 10 with K3 CpG (10 µg), 3'3'/2'3'-cGAMP (1 µg), c-di-GMP (1 µg), DMXAA (50 µg), or OVA (10 µg) comprising or not comprising K3+3'3'/2'3'-cGAMP/c-di-GMP/DMXAA. On day 17, OVA specific sera IgG1 and IgG2c were measured by ELISA. The data is a representation of at least two independent experiments and is shown as the average of two groups+SD. *p<0.05; ** p<0.01 (Mann-Whitney U test).
Figure 3C:
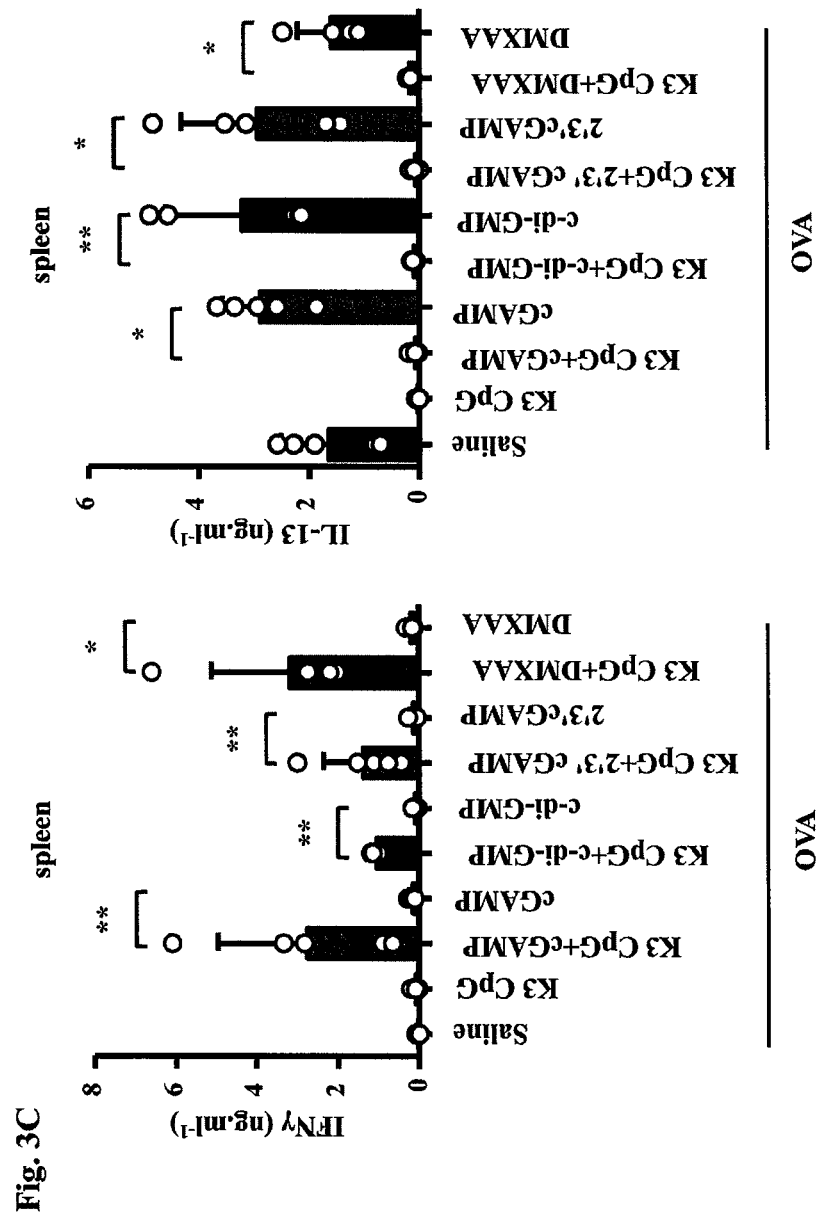
FIG. 3C shows the concentration of IFNγ and IL-13 produced by splenocytes stimulated by OVA. The vertical axis of the left panel indicates the concentration of IFNγ (ng/ml), and the vertical axis of the right panel shows the concentration of IL-13 (ng/ml). Each panel shows results for, from the left, saline, K3 CpG, K3 CpG+3'3'-cGAMP, 3'3'-cGAMP, K3 CpG+c-di-GMP, c-di-GMP, K3 CpG+2'3'-cGAMP, 2'3'-cGAMP, and DMXAA. A combination of a TLR9-agonist and a STING-agonist is a potent type 1 adjuvant that also suppresses type 2 immune responses in vivo. (B—C) mice were immunized intramuscularly on day 0 and day 10 with K3 CpG (10 µg), 3'3'/2'3'-cGAMP (1 µg), c-di-GMP (1 µg), DMXAA (50 µg), or OVA (10 µg) comprising or not comprising K3+3'3'/2'3'-cGAMP/c-di-GMP/DMXAA. Splenocytes were stimulated for 48 hours with OVA (10 µg/ml) protein. Production of IFNγ and IL-13 was measured by ELISA. The data is a representation of at least two independent experiments and is shown as the average of the two groups+SD; *p<0.05, ** p<0.01 (Mann-Whitney U test).
Figure 6:
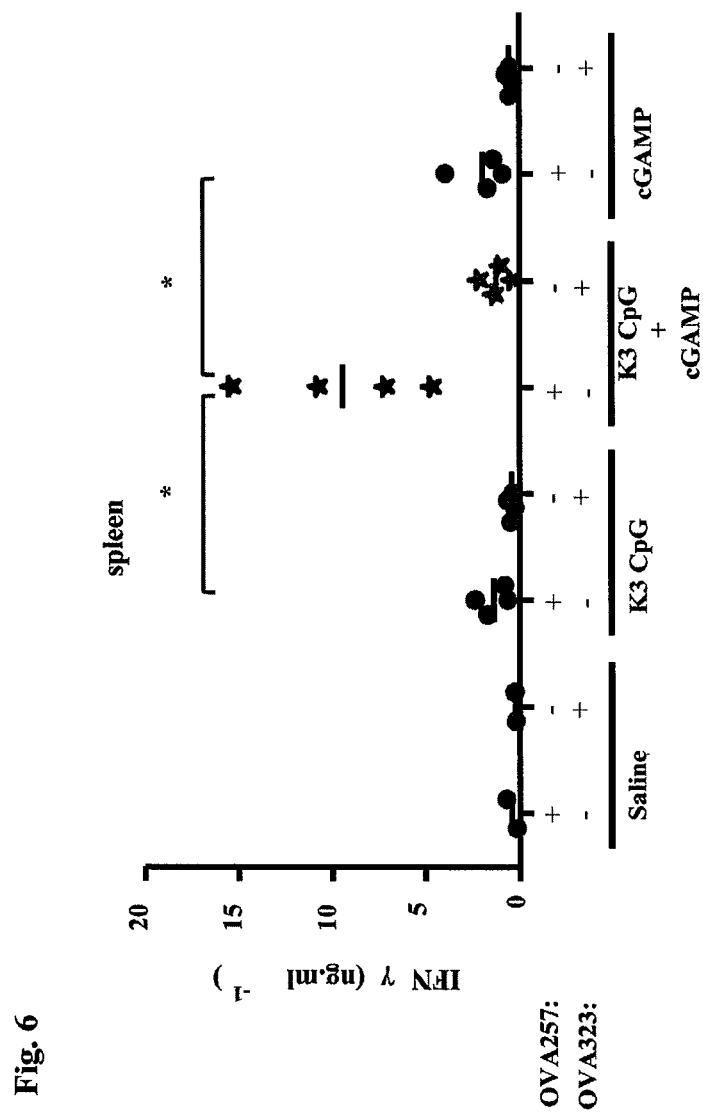
FIG. 6 shows the concentration of IFNγ produced in splenocytes stimulated with OVA254 or OVA323.
Figure 7:
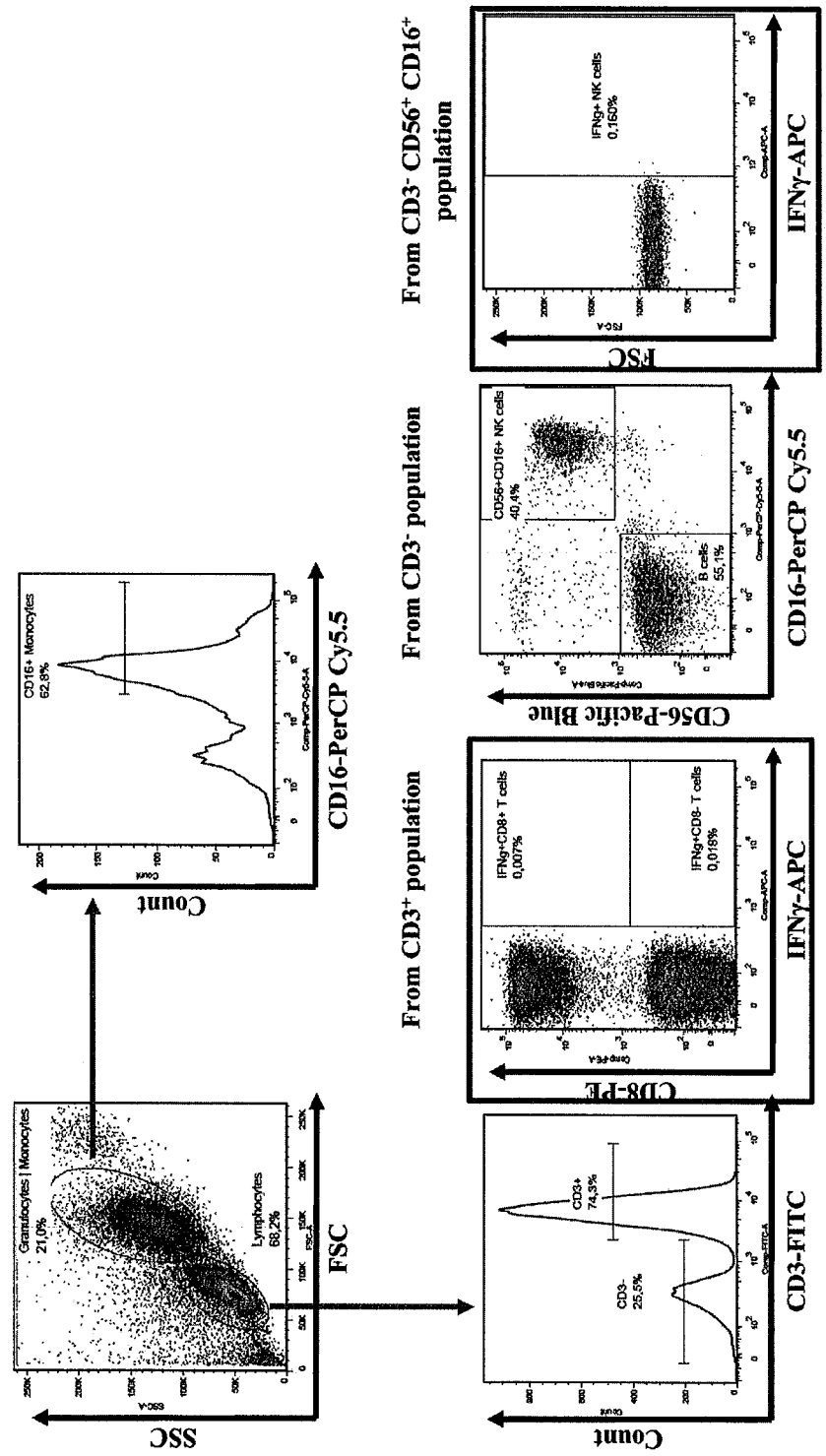
FIG. 7 shows a gating approach for an intracellular IFNγ staining experiment. First, $CD3^{+/-}$ cells were gated from a lymphocyte gate. Next, IFNγ$^+$CD8$^{+/-}$ cells were gated from the $CD3^+$ population. The results thereof are shown. NK cells were gated from the $CD3^-CD56^+CD16^+$ population, and IFNγ$^+$ NK cells are shown in the results.

To evaluate the adjuvant property of these combinations in vivo, the inventors immunized the mice twice on day 0 and day 10 with an OVA protein and K3 CpG, STING-agonist, or a combination of K3 CpG and STING-agonist. On day 17, responses of antigen specific antibodies and splenocytes were tested. All mouse groups adjuvanted with a STING agonist such as cGAMP, c-di-GMP, and DMXAA had a type 2 immune response characterized by high serum anti-OVA IgG1 titer (FIG. 3B) and production of OVA-specific IL-13 by the splenocytes (FIG. 3C), but the group adjuvanted with a TLR9 agonist K3 CpG did not have a type 2 immune response. By sharp contrast, addition of K3 CpG converted all type 2 immune responses induced by a STING agonist into type 1 immune responses characterized by strong induction of OVA specific serum IgG2c and splenocyte IFNγ. The type 2 immune responses are characterized by strong induction of OVA specific serum IgG2c and splenocyte IFNγ, while the production of OVA specific IgG1 and IL-13 is shut down (FIGS. 3B and 3C). The inventors have also observed synergistic induction of IFNγ by OVA specific CD8$^+$ T cells (FIG. 6). These results suggest that a combination of a TLR9-agonist and a STING-agonist induces synergistic adaptable IFNγ in antigen stimulated splenocytes of mice immunized by the combination and induces a potent type 1 adjuvant capable of suppressing type 2 immune responses induced by a STING agonist.

Example 2: Human PBMC Isolation and Stimulation

All hPBMC experiments were conducted in accordance with the approval from the Institutional Review Board of the National Institute of Biomedical Innovation. Human PBMCs were isolated from blood of healthy blood donors using a human lymph separation medium (IBL, Japan). 1×10$^6$ cells were cultured in RPMI. PBMCs were stimulated for 24 hours with K3 CpG (10 μg/ml), cGAMP (10 μM), or K3 CpG+cGAMP. The production of IFNγ was measured by ELISA.

In the in vitro neutralization experiment, hPBMCs cultured as described above were subjected to treatment with IL-12/23p40 neutralizing antibodies (clone: C8.6, BioLegend, San Diego, Calif., USA), type I IFN neutralizing antibodies (clone: MMHAR-2, PBL Interferon Source, Piscataway, N.J., USA), or IL-12/23p40 neutralizing antibodies and type I IFN neutralizing antibodies (5 μg/ml) 24 hours before stimulation for 30 minutes.

(Results: K3 CpG and cGAMP, when Combined, Potently Induce IFNγ in Human PBMCs (hPBMCs))

K3 CpG is a humanized type K (also known as type B) CpG ODN reported to induce type 1 immune responses, but only weakly induces IFN [Klinman et al., Nat. Rev. Immunol. (2004) 4: 1-10; Verthelyi et al., J. Immunol. (2001) 166: 2372-2377]. Meanwhile, it has been reported that cGAMP can strongly induce type 1 IFN and functions as an adjuvant [Li et al., Science. (2013) 341: 1390-4], while other STING agonists induce type 2 immune responses [Tang et al., PLoS One. (2013) 8: 1-6]. To overcome such known limitations of K3 CpG and cGAMP, the inventors investigated the immunostimulatory property of a combination of K3 CpG and standard 3'3'-cGAMP in hPBMCs in vitro. In order to find the interaction between a TLR9-mediated signaling pathway and a STING-mediated signaling pathway, multiple hPBMCs were used to screen many cytokines (data not shown). The inventors then discovered that the combination of the invention exhibits potent synergy (about 10 to 90 fold relative to stimulation with K3 CpG or cGAMP alone) in inducing IFNγ (FIG. 1A).

Next, in order to identify the major IFNγ producing cell types in hPBMCs, the inventors have performed intracellular staining of IFNγ in hPBMCs that were stimulated with K3 CpG, CGAMP, or a combination thereof. The results of the inventors show that among hPBMCs, CD3$^-$CD56$^+$CD16$^+$ NK cells are major synergistic IFNγ producing cells in response to a stimulation of a combination (FIG. 1B).

Figure 1C:
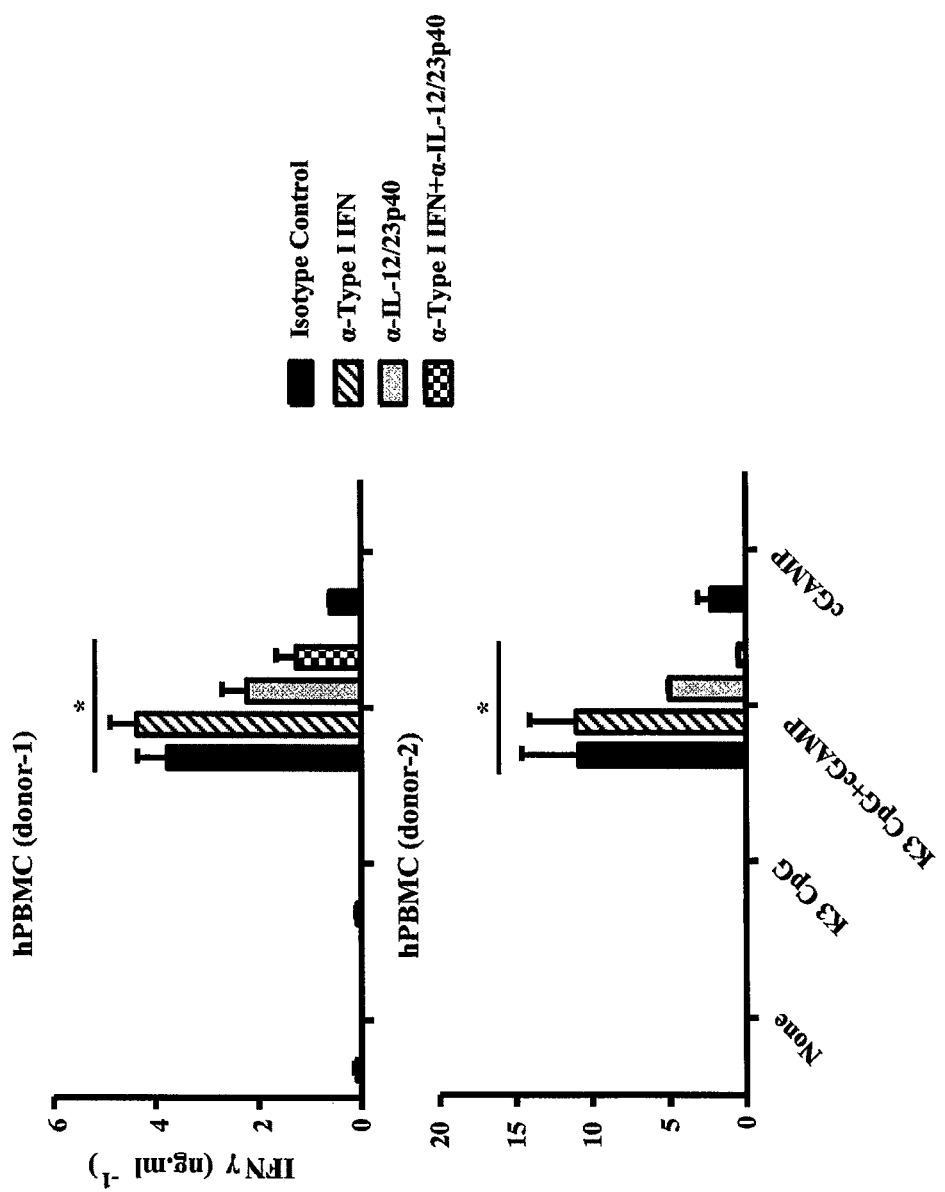
FIG. 1C shows the concentration of IFNγ produced in the supernatant of human PBMC culture of each donor when treated with a neutralizing antibody.

In addition of inducing type 1 immune responses, type I IFN and IL-12 can activate NK cells for producing IFNγ [Hunter et al., Immunol. Lett. (1997) 59: 1-5; Nguyen et al., J. Immunol. (2002) 169: 4279-4287]. Thus, the inventors have examined the role of IL-12 and type I IFN in the production of congenital IFNγ which is induced by the combination in hPBMCs. Treatment with IL-12 neutralizing antibodies reduced synergistic IFNγ induction by a stimulation of the combination (FIG. 1C). While treatment with type I IFN neutralizing antibodies had no effect on the production of IFNγ induced by the combination, simultaneous neutralization of both type I IFN and IL-12 further reduced synergistic IFNγ production (FIG. 1C). These results show that IL-12, in combination with type I IFN, is useful in synergistic production of IFNγ by hPBMCs. In summary of the above-described results, K3 CpG and cGAMP, when combined, can be potent NK activating agents inducing the production of a large quantity of IFNγ via a mechanism that is partially dependent on IL-12 and type I IFN.

Example 3: Culture of Mouse PBMCs and Dendritic Cells

Mouse PBMCs were isolated from C57BL/6J mice using mouse lymph separation medium (IBL, Japan). 0.5×10$^6$ cells were cultured in RPMI. Bone marrow cells from the tibia and the femur of C57BL/6J mice was washed off from the GM-DC culture. These cells were prepared by culturing for 7 days in the presence of 20 ng/ml of GM-CSF (Pepro Tech, Rocky Hill, N.J., USA). GM-DCs were cultured in RPMI containing 1% penicillin/streptomycin and 20% FCS. FL-DC culture was prepared from bone marrow cells of C57BL/6J mice cultured for 7 days in the presence of 100 ng/ml of human Flt3L (Pepro Tech). FL-DCs were cultured in RPMI containing 1% penicillin/streptomycin and 10% FCS.

Mouse PBMCs derived from wild-type mice and IRF3/7 DKO mice were stimulated for 24 hours with K3 CpG, cCAMP, or K3 CpG+cGAMP to measure the IFNγ production by ELISA. Further, GM-DCs and FL-DCs were stimulated for 24 hours with K3 CpG, cGAMP, or K3 CpG+cGAMP to measure the production of IL-12940 and IFNα by ELISA.

(Results: Cellular Mechanism and Intracellular Mechanism of Synergistic IFNγ Induction by K3 CpG and cGAMP in Mice)

To investigate the synergy between the TLR9 agonist and STING-agonist of the invention on induction of early (congenital) IFNγ in mice, the inventors stimulated mouse PBMCs (mPBMCs) with K3 CpG, cGAMP, or a combination thereof in vitro. The inventors observed a large amount of IFNγ production in a similar synergistic way observed in hPBMCs. Since IRF3 and IRF7 are downstream molecules required for inducing cGAMP mediated type I IFN and CpG mediated type I IFN, respectively [Wu et al., Science. (2013) 339: 826-30; Kawai et al., Nat. Immunol. (2004) 5: 1061-8], the inventors used mPBMCs derived from wild-type mice or mice with deletions of both IRF3 and IRF7 (double knock-out, DKO) to study the role of IRF3 and IRF7 in synergistic IFNγ production. Synergistic IFNγ production was suppressed in IRF3/7 DKO mPBMCs (FIG. 2A).

Since IL-12 and type I IFN are the causes of synergistic IFNγ production in hPBMCs (FIG. 1C), the inventors studied the ability of combined K3 CPG and cGAMP which activates dendritic cells that canto produce IL-12 and/or type I IFN. When the inventors incubated GM-CSF derived dendritic cells (GM-DC) and Flt3L derived dendritic cells (FL-DC) with K3 CpG, cGAMP, or a combination thereof, the inventors found the same synergy as that observed in mPBMCs (FIGS. 2B to 2D). The combination of K3 CpG and cGAMP induced significantly higher IL-12p40 production by both GM-DCs (FIG. 2B) and FL-DCs (FIG. 2C) and significantly higher IFNα production by FL-DCs (FIG. 2D) than the amount induced solely from stimulation. This shows the potential role of IL-12 and type I IFN in the synergistic IFNγ induction by the combination of the invention. Together, these results indicate that the synergy between K3 CpG and cGAMP, which potently induces IFNγ in hPBMCs, is reproduced in mice. The mechanism of synergy involves IRF3/7 mediated intracellular signaling, and the synergy induces production of type I IFN by plasma cell-like DCs (pDC) and IL-12 by both classical DCs (cDCs) and pDCs.

Example 5: Staining of Intracellular Cytokines and Cell Surface Molecules

Human PBMCs were stimulated for 16 hours with K3 CpG (10 μg/ml), cGAMP (10 μM), or K3 CpG+cGAMP and were stimulated in the presence of Brefeldin A for the last 4 hours. After the stimulation, the cells were collected to stain the surface molecules using CD16-PerCP-Cy5.5 antibodies (BD Biosciences: Franklin Lake, N.J.), CD56-BV421 antibodies (BioLegend), CD3-FITC antibodies (BD Biosciences), and CD8-PE antibodies (Miltenyi Biotech). The immobilized and permeabilized cells were stained with IFNγ-APC (BioLegend) for detection of intracellular IFNγ and analyzed using BD FACSCANTO II flow cytometer.

Example 6: Tumor Cells and Treatment

E. G7-OVA thymoma cells were purchased from American Type Culture Collection (VA, USA) and were cultured in RPMI. $1 \times 10^6$ cells were subcutaneously injected into the back of mice on day 0. On day 7 and day 10, mice were given PBS (50 μl), K3 CpG (10 μg), cGAMP (I0 μg), or K3CpG+cGAMP in the tumor. The mice were monitored for the growth of tumor for 22 days.

(Results: K3 CpG and cGAMP can Together Suppress Tumor Growth in Mouse Isologous Explant Tumor Model)

Figure 5:
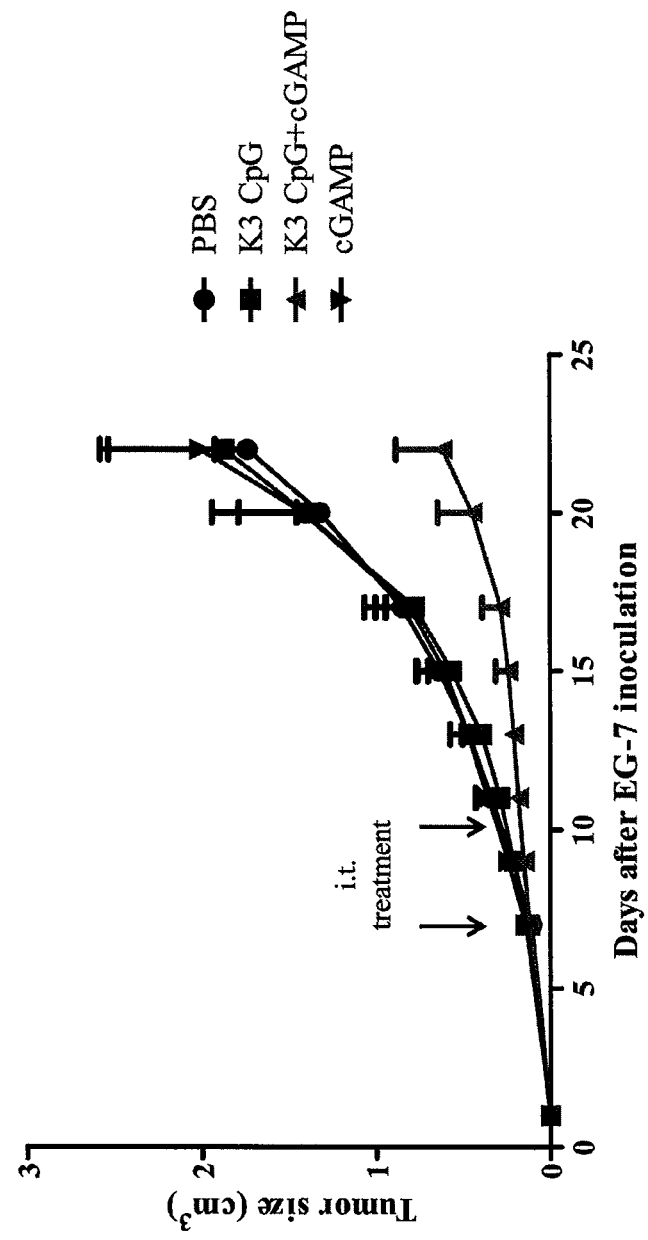
FIG. 5 shows a graph that measures tumor growth in an EG-7 mouse tumor model. The vertical axis indicates the tumor size ($cm^3$), and the horizontal axis indicates the number of days after inoculation of EG-7 lymphoma cells. The combination of K3 CpG and cGAMP effectively suppresses tumor in EG-7 mouse tumor models. Mice were subcutaneously injected with $1\times10^6$ EG-7 lymphoma cells (in 100 μl of PBS) on day 0. On day 7 and day 10, the mice were subjected to intratumor injection of PBS (n=8), K3 CpG (n=8), cGAMP (n=8), or K3 CpG cGAMP (n=9). The mice were monitored for 22 days for the growth of tumor. The data is a representation of at least two independent experiments.*$p<0.05$; ** $p<0.01$ (Mann-Whitney U test).

Since Th1 cell and CD8+ T cell responses are important for the refinement of antitumor immunity, the inventors studied the immunotherapeutic potential of the combination of K3 CpG and cGAMP in mouse tumor models. The inventors inoculated mice with OVA expressing EG-7 lymphoma cells by subcutaneous injection. On day 7 and day 10, mice were subjected to intratumor injection of PBS, K3 CpG (10 μg), cGAMP (10 μg), or K3 CpG and cGAMP. The combined treatment significantly suppresses tumor growth compared to PBS, K3 CpG, or cGAMP treatment (FIG. 5). This suggests that the combination of the invention can function as an immunotherapeutic agent for cancer that is free of antigens.

Example 7: IFNγ Production in KO Mice

Wild-type Tmem173gt, IRF3/7 DKO, MyD88 KO, and IFNAR KO C57BL/6J mice were immunized via an intramuscular route on day 0 and day 10 with OVA and K3 CpG, cGAMP, or K3 CpG+cGAMP. On day 17, OVA specific serum IgG2c and IgG1 were measured by ELISA. Further, splenocytes were stimulated for 48 hours with OVA to measure IFNγ production by ELISA.

IL-12p40+/− and −/− C57BL/6J mice were also immunized via an intramuscular route on day 0 and day 10 with OVA and K3 CpG, cGAMP, or K3 CpG+cGAMP. On day 17, OVA specific sera IgG2c and IgG1 were measured by ELISA. Further, splenocytes were stimulated for 48 hours with an OVA protein to measure IFNγ production by ELISA.

(Results: Synergistic Induction of IFNγ Dependent on IRF3/7, STING, MyD88, IL-12, and Type I IFN Signaling)

Figure 4A:
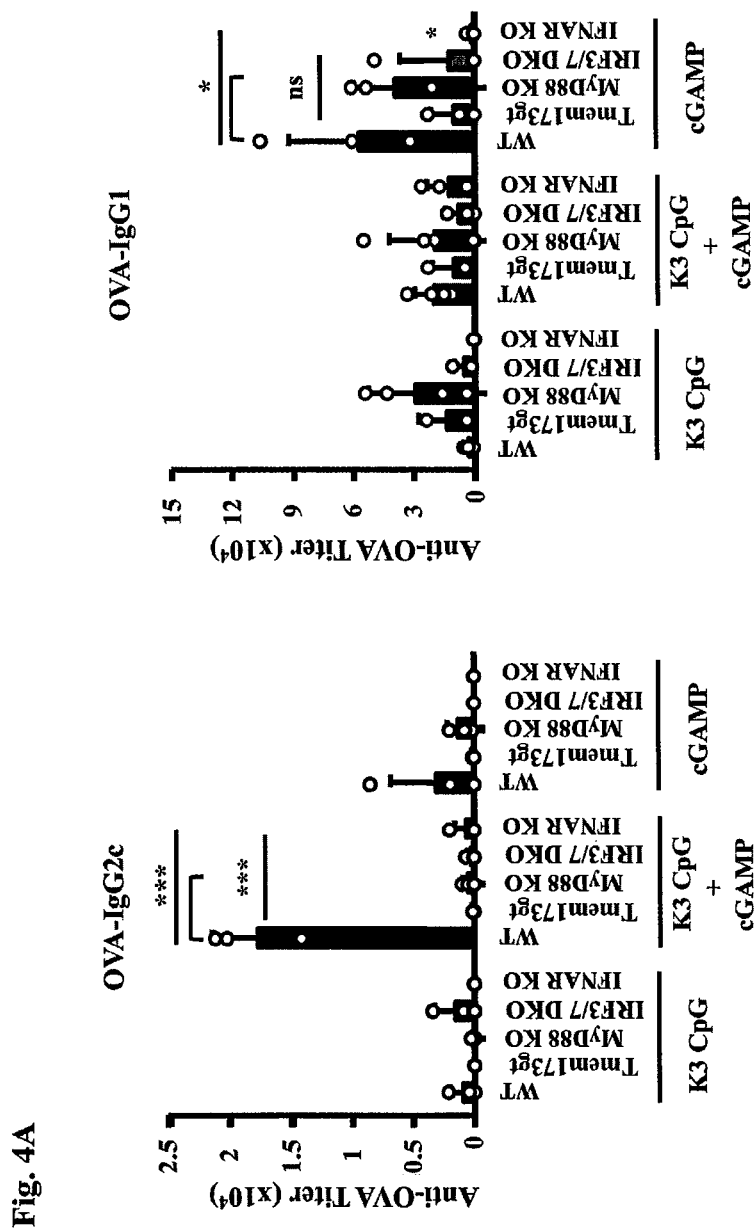
FIG. 4A shows the anti-OVA antibody titer of the serum in each mice immunized with OVA. The left panel shows the anti-OVA antibody titer of IgG2c, and the right panel shows the anti-OVA antibody titer of IgG1. Each panel shows the results for, from the left group, K3 CpG, K3 CpG+cGAMP, and cGAMP.
Figure 4B:
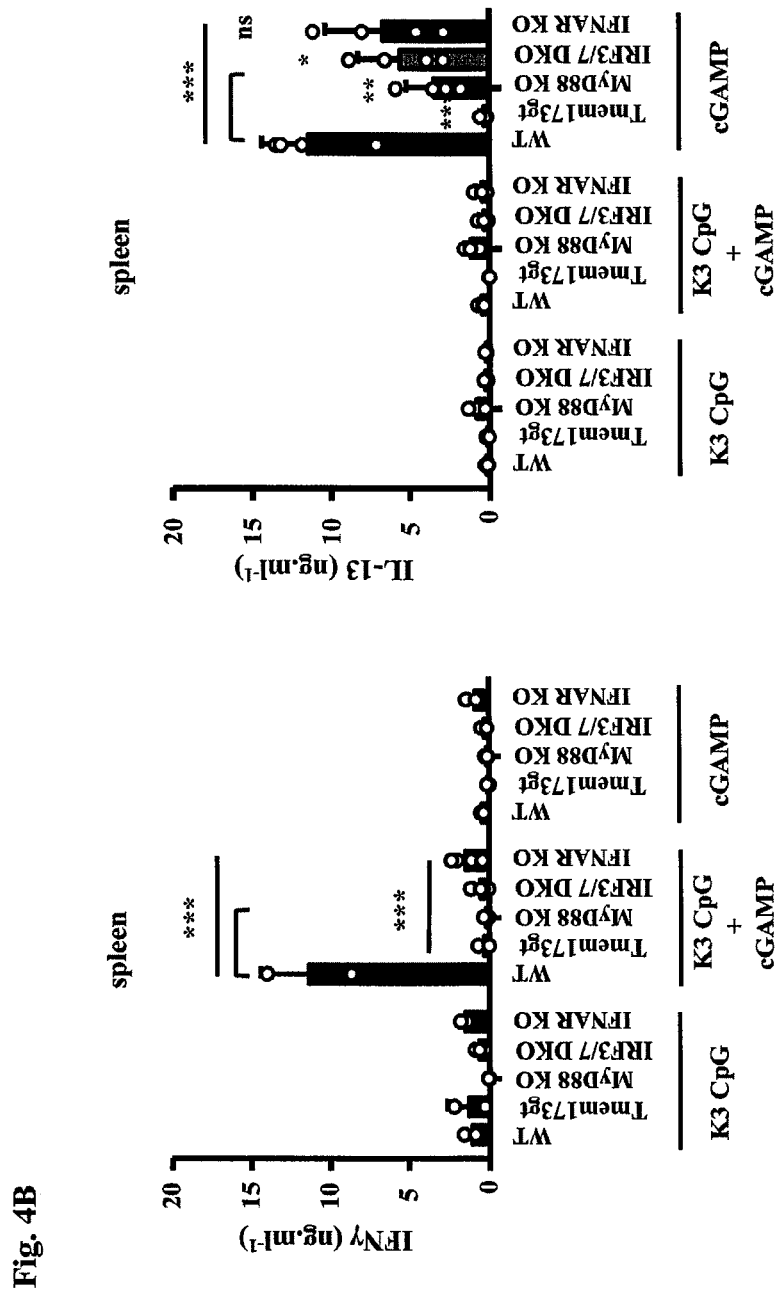
FIG. 4B shows the concentration of IFNγ and IL-13 produced in splenocytes stimulated with OVA. The vertical axis of the left panel indicates the concentration of IFNγ (ng/ml), and the vertical axis of the right panel indicates the concentration of IL-13 (ng/ml). Each panel shows results for, from the left group, K3 CpG, K3 CpG+cGAMP, and cGAMP.

The inventors demonstrated that synergistic production of congenital IFNγ in mPBMCs is completely dependent on IRF3 and IRF7 that are required for induction of type I IFN by each of cGAMP and K3 CpG. Since cGAMP is a ligand of STING and K3 CpG is a ligand of TLR9 that signals via the adapter molecule MyD88, the inventors used IRF3/7 DKO mice, IFNα/β receptor (IFNAR) KO mice, MyD88 KO mice, and STING mutant mice to assess the involvement of IRF3/7, MyD88, STING, and type I IFN in the synergistic production of antigen specific IFNγ induced by the combination. The production of IFNγ by the spleen and antigen specific IgG2c induced by the combination in the serum was significantly reduced in STING mutant mice, IRF3/7 DKO mice, MyD88 KO mice, and IFNAR KO mice relative to wild-type mice (FIGS. 4A and 4B).

Figure 4C:
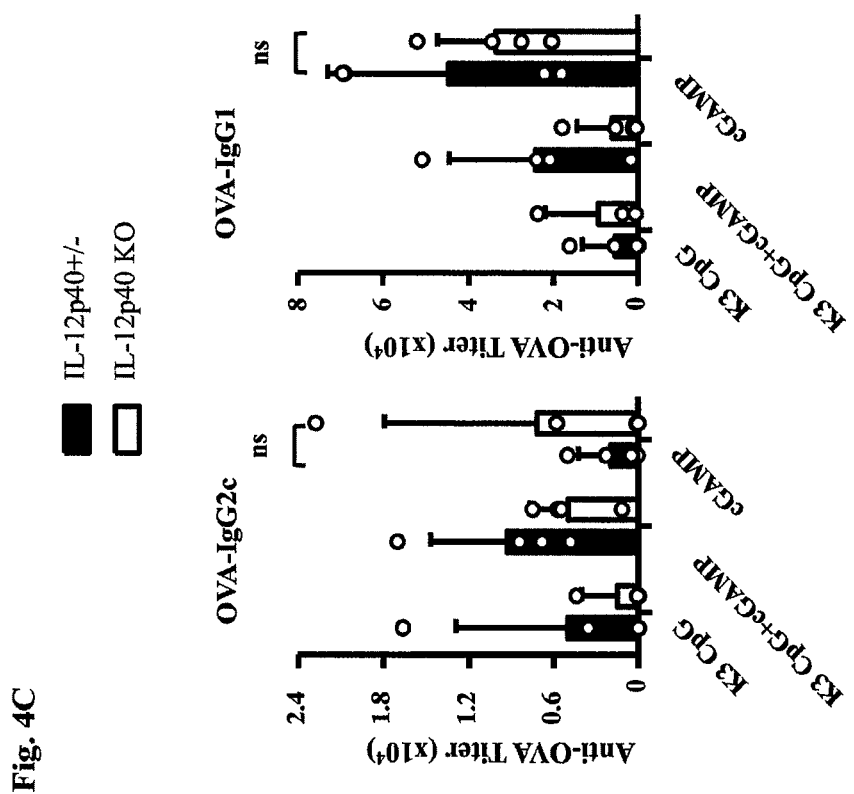
FIG. 4C shows the anti-OVA antibody titer of the serum in C57BL/6J mice immunized with OVA. The left panel shows the anti-OVA antibody titer of IgG2c, and the right panel shows the anti-OVA antibody titer of IgG1. Each panel shows results for, from the left group, K3 CpG, K3 CpG+ cGAMP, and cGAMP. The left side of each group shows IL-12p40+/−, and the right side shows IL-12p40 KO. The synergistic effect of the combination of K3 CpG and cGAMP in induction of antigen-specific IFNγ is dependent on IRF3/7, STING, MyD88, IL-12, and type I IFN signaling. The (C) IL-12p40+/− and −/−C57BL/6J mice were immunized with OVA and K3 CpG, cGAMP, or K3 CpG+cGAMP via the intramuscular route on day 0 and day 10. On day 17, OVA specific sera IgG2c and IgG1 were measured by ELISA. The data is a representation of at least two independent experiments and is shown as the average of two groups+SD.
Figure 4D:
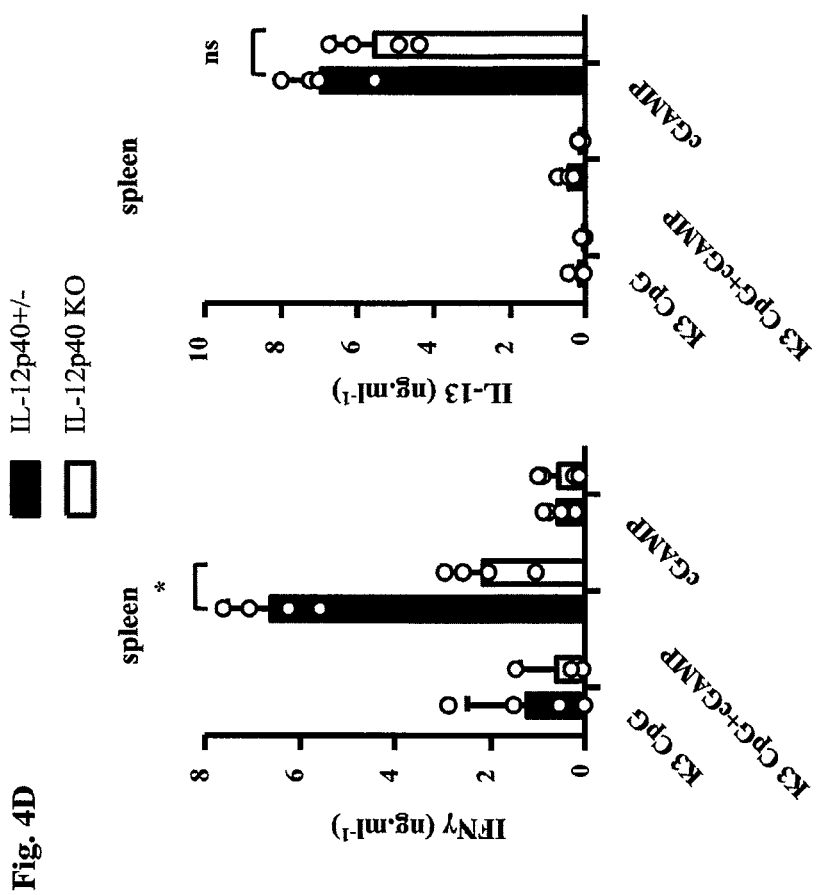
FIG. 4D shows the concentration of IFNγ and IL-13 produced in splenocytes stimulated with OVA. The vertical axis of the left panel indicates the concentration of IFNγ (ng/ml), and the vertical axis of the right panel indicates the concentration of IL-13 (ng/ml). Each panel shows the results for, from the left group, K3 CpG, K3 CpG+cGAMP, and cGAMP. The left side of each group shows results for IL-12p40+/−, and the right side shows the results for IL-12p40 KO. The synergistic effect of the combination of K3 CpG and cGAMP in the induction of antigen-specific IFNγ is dependent on IRF3/7, STING, MyD88, IL-12, and type I IFN signaling. (D) The splenocytes were stimulated for 48 hours with OVA proteins. The production of IFNγ was measured by ELISA. The data is a representation of at least two independent experiments and is shown as the average of the two groups+SD; *$p<0.05$, ** $p<0.05$ (Mann-Whitney U test).

The in vitro study of the inventors with mouse and human PBMCs also showed that IL-12 contributes to the synergistic induction of congenital IFNγ. Thus, the inventors investigated the involvement of IL-12 by using IL-12p40+/− mice and −/− mice. The inventors discovered that IL-12p40 is not needed for the induction of an IgG2c antibody response, although IL-12p40 is required for synergistic induction of antigen specific IFNγ (FIGS. 4C and 4D). All of the results of the inventors suggest that the combination of K3 CpG and cGAMP is a potent type 1 adjuvant, which synergistically induces the production of antigen specific IFNγ in a IRF3/7, STING, MyD88, IL-12, and type I IFN signaling dependent manner.

Example 9: Measurement of IgE Antibody Production

This is an Example for allergy suppression.

After anesthesia, mice were intramuscularly immunized on day 0 and day 10 with OVA (10 μg), OVA and K3 CpG (10 μg), cGAMP (10 μM), or K3 CpG GAMP. On day 17, OVA specific serum IgE was measured by ELISA.

(Results: STING Agonists Induce IgE, but this is Suppressed by Combination Thereof with CpG).

Figure 8:
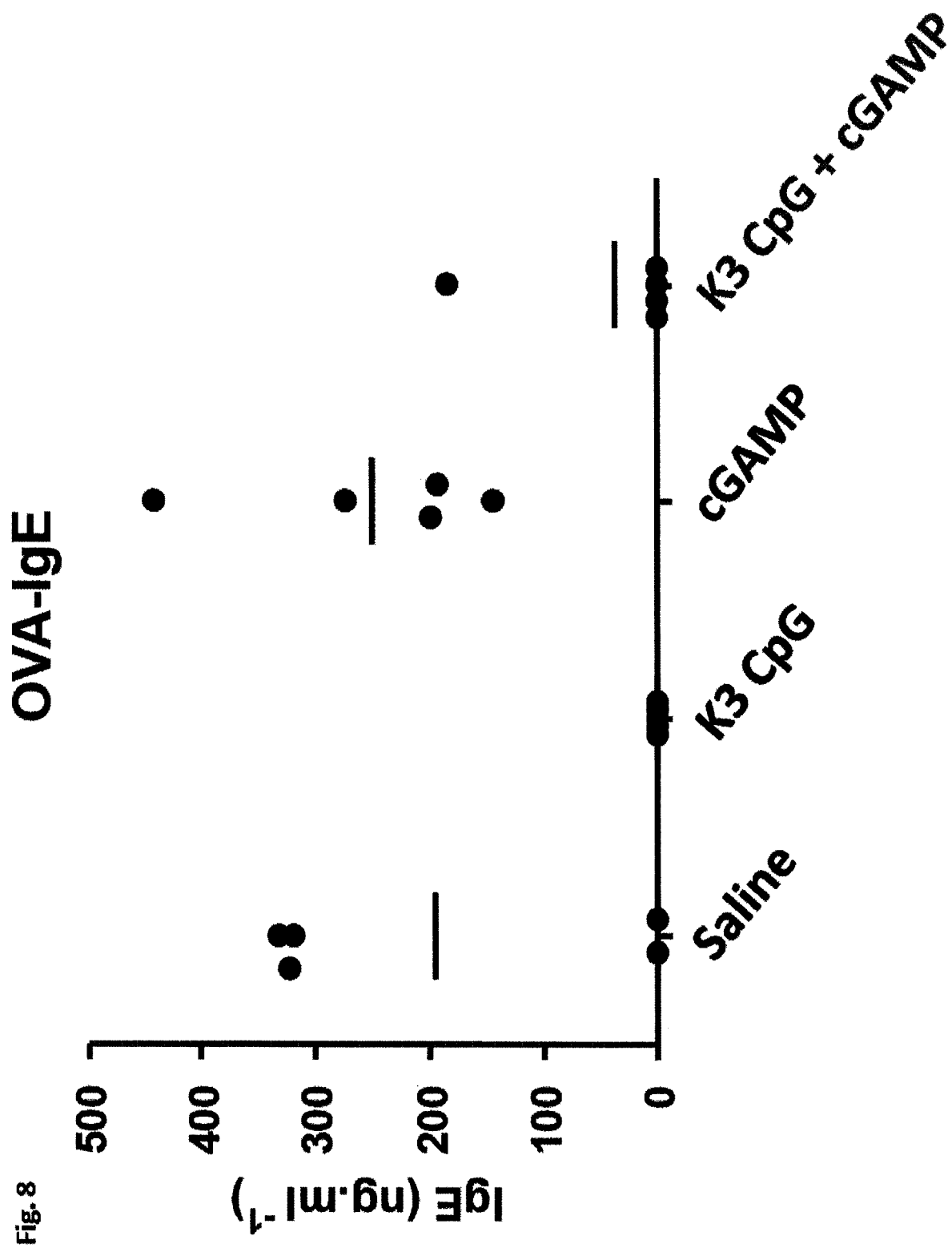
FIG. 8 shows the concentration of IgE of the serum in mice immunized with OVA.
Figure 9:
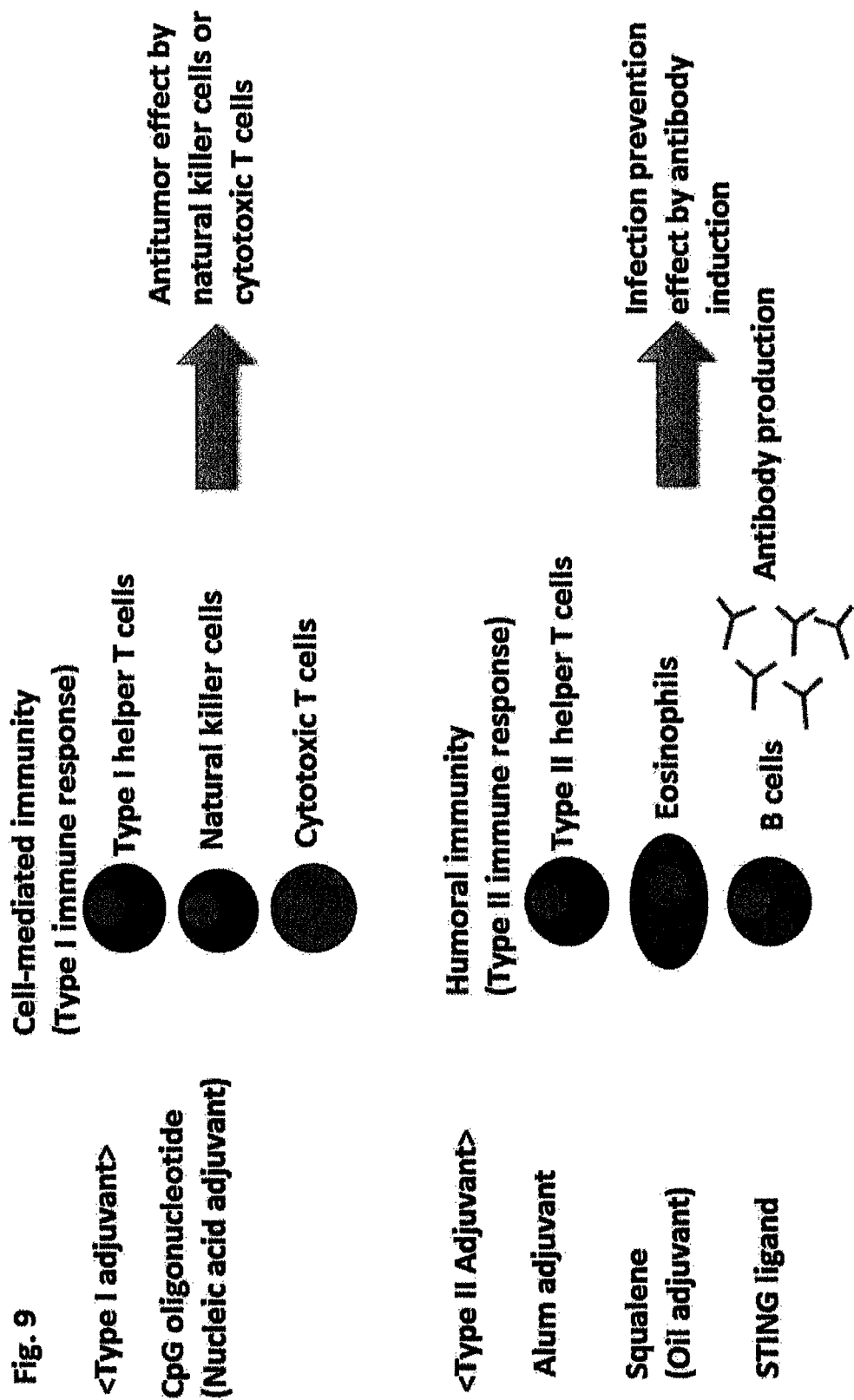
FIG. 9 shows a summary of cell-mediated immunity and humoral immunity. Many vaccine adjuvants have mainly been developed to induce antibody production (humoral immunity) up to this point. Many of the current adjuvants, including alum adjuvants, are therefore humoral immunity inducing adjuvants called Th2 adjuvants (type II adjuvants). However, induction of cell-mediated immunity is more important than humoral immunity in the prevention or therapy of cancer or allergies. Such adjuvants are called Th1 adjuvants (type I adjuvants).
Figure 10:
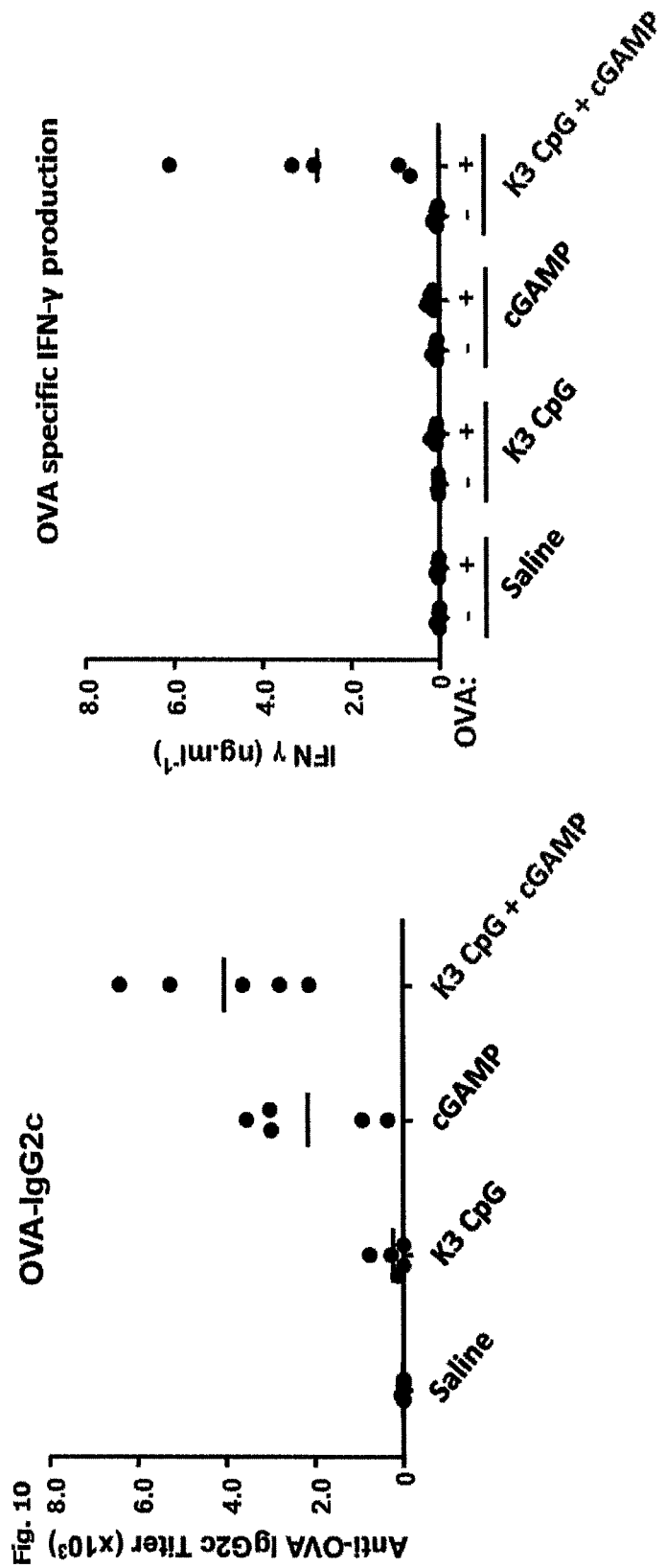
FIG. 10 shows indicators for type I adjuvants, i.e., IgG2c and IFNγ production. The left panel shows the anti-OVA IgG2c titer of the serum in mice immunized with OVA. The left panel shows results for, from the left, saline, K3 CpG, cGAMP, and K3 CpG+cGAMP. The right panel shows IFNγ production with stimulation with OVA or without simulation with OVA. The right panel shows results for, from the left group, saline, K3 CpG, c GAMP, and K3 CpG+cGAMP. The left side of each group shows IFNγ produced without the stimulation with OVA, and the right side shows IFNγ produced with the stimulation with OVA. The vertical axis indicates the concentration of IFNγ (ng/ml). The combination of CpG ODN and a STING agonist synergistically induces a Th1 immune response.
Figure 11:
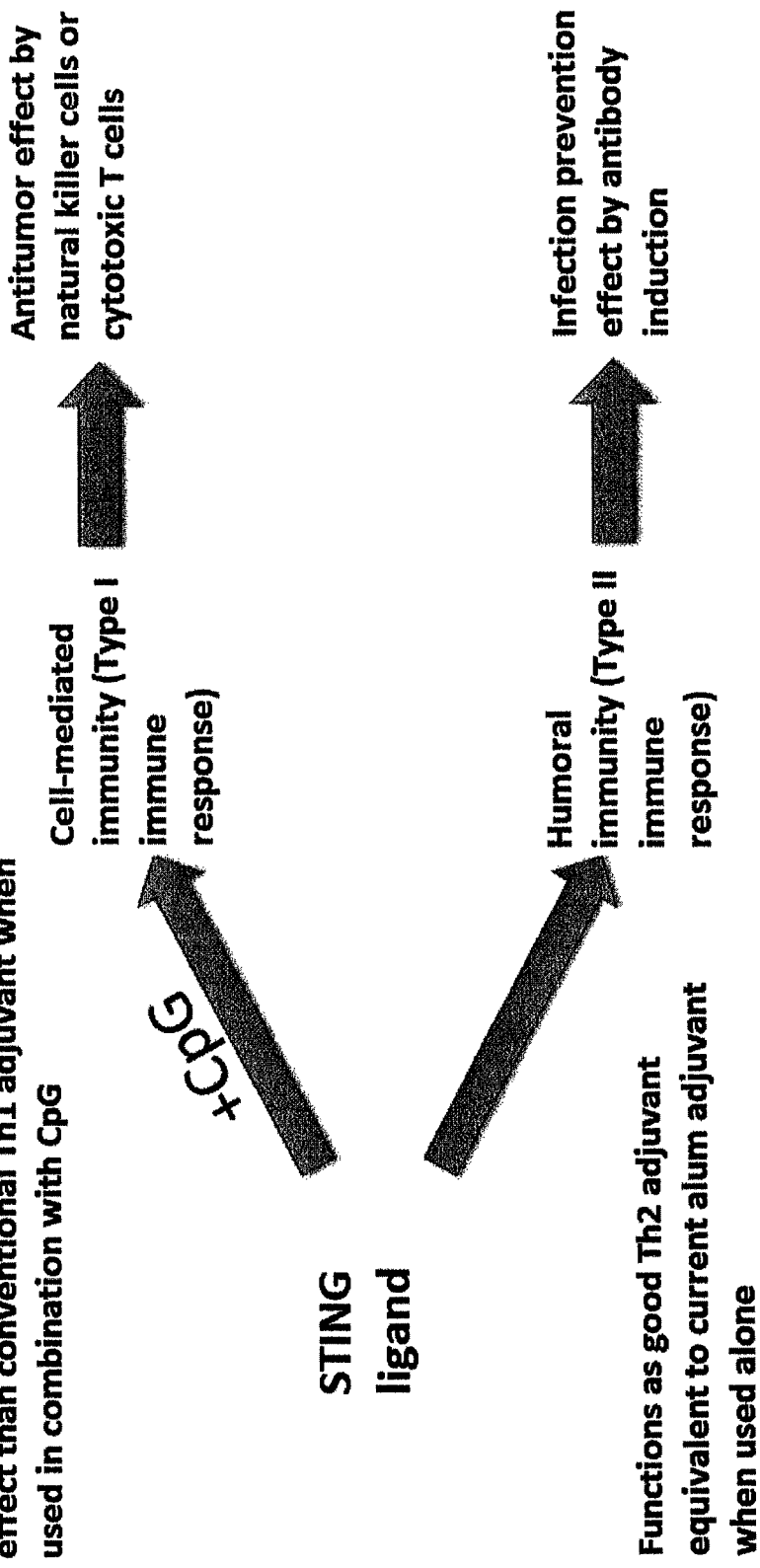
FIG. 11 shows a summary of a novel next-generation adjuvant, which was formulated based on a STING agonist. STING agonists themselves, including DMXAA, function as TH2 adjuvants that activate humoral immunity, as in alum adjuvants. Thus, a STING agonist, when used as a platform, can be used as a conventional humoral immunity inducing Th2 adjuvant when used directly or as a potent cell-mediated immunity inducing Th1 adjuvant when combined with CpG ODN.

Many of the current adjuvants are Th2 adjuvants inducing antibody production. Meanwhile, such adjuvants were unsuited for vaccine therapy on cancer or allergy. Furthermore, STING agonists induce IgE as a side effect. Thus, there is a risk of inducing allergic inflammation. However, the present invention can induce a potent Th1 adjuvant effect while suppressing IgE induction by simply combining two types of adjuvants (FIG. 8).

(Discussion)

Vaccines that are effective against an intracellular pathogen or cancer require an adjuvant that induces a type 1 immune response. Cyclic dinucleotides such as cGAMP and c-di-GMP directly bind to a transmembrane molecule STING and activate a TBK1-IRF3 dependent signaling pathway to induce type I IFN. Thus, cyclic dinucleotides have drawn attention as potential vaccine adjuvants [Dubensky et al., Ther. Adv. Vaccines. (2013) 1: 131-143]. However, evidence that STING-agonists induce type 2 immune responses instead of type 1 protective immune responses [Tang et al., PLoS One. (2013) 8: 1-6] suggests that their potential therapeutic application is limited. In this study, the inventors solve this problem by combining a STING-agonist with a TLR9 ligand, K3 CpG. This combination synergistically enhances the production of congenital IFNγ and adaptive IFNγ. This combination functions as a potent type 1 adjuvant, strongly induces antibodies and $CD4^+$ Th1 cells and $CD8^+$ T cells, and functions as an anti-tumor agent that can effectively suppress tumor growth in mouse tumor models.

This study demonstrates that the combination of K3 CpG and cGAMP synergistically induces the production of congenital IFNγ in both human and mouse PBMCs (FIGS. 1 and 2), suggesting that this phenomenon is conserved between humans and mice. The in vitro results obtained by the inventors also demonstrate that the action mechanism is associated with IL-12 and type I IFN. Specifically, during synergy between K3 CpG and cGAMP, type I IFN was not required as the loss of its effect was compensated by IL-12 (FIG. 1C). Previous reports suggested that type IFN and IL-12, after *Listeria monocytogenes* infection, can synergistically induce the production of IFNγ by $CD4^+$ T cells. While they demonstrated that synergy was significantly reduced in the absence of both cytokines, synergy was partially reduced in the absence of one of the cytokines, which is in agreement with the results obtained by the inventors [Way et al., Immunol. (2007) 178: 4498-4505]. As in the synergy observed in PBMCs, the combination of the invention can synergistically induce the production of IL-12p40 in GM-DCs and FL-DCs (FIGS. 2C and 2D), suggesting a potential role served by normal dendritic cells and plasma cell-like dendritic cells on synergy induced by the combination. Similar synergy of IL-12 has been reported by Krummen et al. by a combination of poly I:C and TLR ligand CpG in bone marrow derived DCs requiring MyD88 and TRIF dependent signaling pathway [Krummen et al., J. Leukoc. Biol. (2010) 88: 189-99]. The results obtained by the inventors also suggest that a combination of molecules that activate MyD88 dependent (TLR9) and non-dependent (STING) signaling pathways produces a strong immunostimulatory agent, and such a combination can be useful in immunotherapeutic applications.

According to the findings of the inventors, NK cells are the main IFNγ producing cells in culture of hPBMCs and the subsequent stimulation by the combination (FIG. 1B). Meanwhile, previous reports demonstrate that NK cells express TLR9 at a low level, but cells responding to a stimulation of CpG are TLR9 expressing pDCs and B cells in hPBMCs. It is also reported that IL-12 and type I IFN regulate cytotoxicity and production of IFNγ in NK cells [Nguyen et al., J. Immunol. (2002) 169: 4279-4287; Chace et al., Clin. Immunol. Immunopathol (1997) 84: 185-193]. Considering these reports and the in vitro data of the inventors, the mechanism of synergistic induction of congenital IFNγ proposed by the inventors consists of pDCs responding to K3 CpG and cDCs or other cells such as macrophage responding to cGAMP such that a large quantity of type I IFN and IL-12 can be produced. The mechanism subsequently performs signaling via an IL-12 receptor and type I IFN receptor and cooperate to induce the production of IFNγ in NK cells.

The first report regarding the adjuvant effect of 2'3'-cGAMP showed that intramuscular cGAMP immunization can induce antigen specific B cell and T cell responses in a STING dependent manner [Li et al., Science. (2013) 341: 1390-4]. The in vivo immunization studies of the inventors using 3'3'-cGAMP are also consistent with the previous reports, which is induction of strong antigen-specific B cell and T cell response in a STING-dependent manner (FIGS. 4A and 4B). The inventors also demonstrated that 3' 3'-cGAMP is a type 2 adjuvant that can induce not only IgG1, but also IgG2c antibody responses and Th2 cytokine responses in splenocytes (FIGS. 3B and 3C). Type 2 adjuvants generally do not induce the production of Th1-like Ig isotype (IgG2c). However, type I IFN induces IgG2c antibody responses. Thus, cGAMP can induce Th1-like Ig isotype, likely due to the ability to induce type I IFN [Swanson et al., J. Exp. Med. (2010) 207: 1485-500]. Furthermore, the inventors have discovered that a separate mechanism is involved in the induction of B cell and T cell responses by cGAMP, and a cGAMP induced antibody responses are dependent on type I IFN signaling, but Th2 responses are not dependent thereon in this mechanism (FIG. 4B). Furthermore, it is known that cGAMP induces the production of type I IFN by signaling via only the STING-IRF3 axis [Wu et al., Science. (2013) 339: 826-30]. Thus, the inventors predicted that a reduction in antibody and T cell responses in IRF3/7 DKO mice would be observed. However, cGAMP induced antibody responses slightly decreased in IRF3/7 DKO mice, while cGAMP induced T cell responses were partially dependent on IRF3/7 and surprisingly dependent on MyD88. Such an effect was completely dependent on STING (FIGS. 4A and 4B). Thus, in addition to the STING-IRF3 pathway, the inventors are further investigating the possibility that cGAMP can activate an unknown signaling pathway involving the adapter molecule MyD88.

K3 CpG had been reported as an adjuvant capable of inducing type 1 immune responses [Chu et al., J. Exp. Med. (1997) 186: 1623-1631], but the inventors discovered that K3 CpG is a type 1 adjuvant that is weak by itself because K3 CpG cannot induce antigen specific antibody or T cell responses at a level comparable to cGAMP or immunization group by the combination. Interestingly, a combination of weak type 1 adjuvant K3 CpG with a type 2 adjuvant cGAMP resulted in a strong type 1 adjuvant that induces synergistic production of antigen specific IFNγ and strong Th1-like antibody and $CD8^+$ T cell responses (FIGS. 3 and 6). The discovery of the inventors is also consistent with the previous study showing that the combination of a type 2 adjuvant CpG and IFA induces type 1 immune responses while suppressing type 2 immune responses [Chu et al., J. Exp. Med. (1997) 186: 1623-1631]. Importantly, the inventors demonstrated that the combination of the invention can suppress type 2 immune responses induced by cGAMP in addition to inducing potent type 1 immune responses. This is important in terms of increased safety, as predominant type 2 responses are reported as inducing many chronic diseases such as allergies [Spellberg et al., Clin. Infect. Dis. (2001) 90509: 76-102; Muller et al., J. Immunol. (1993) 150: 5576-5584; Seki et al., Nat. Med. (2003) 9: 1047-1054]. The results obtained by the inventors are also consistent with the discovery of Lin et al. in that IgG2c production is increased while IgG1 production is suppressed by CpG [Lin et al., Eur. J. Immunol. (2004) 34: 1483-7]. Furthermore, the synergistic effect of the combination of the invention on antigen specific IFNγ induction is dependent on IRF3 and IRF7 (FIG. 4A and FIG. 4B), indicating that type I IFN may play an important role in the synergy. This concept is further supported by the complete elimination of synergy observed in IFNAR KO mice by the inventors (FIGS. 4A and 4B). Furthermore, MyD88 is a downstream signaling molecule of TLR9 and cGAMP is a ligand of STING. Thus, the inventors discovered that the type 1 immunization inducing effect of the combination is dependent on both MyD88 and STING as expected (FIGS. 4A and 4B). On the other hand, the inventors have demonstrated that IL-12p40 is required for synergistic induction of Th1 cytokine responses, but not for induction of IgG2c antibody responses (FIGS. 4C and 4D). IL-12 is important in the generation of Th1 cells and production of IFNγ. Thus, it is logical that dependency of IL-12 in Th1 cytokine responses is observed. The conceivable explanation for the IL-12 non-dependent IgG2c induction by the combination of the invention is that the production of type I IFN in KO mice can compensate for the absence of IL-12. In previous reports, type I IFN can induce IgG2c antibody responses in a T cell non-dependent manner [Swanson et al., J. Exp. Med. (2010) 207: 1485-500], while IL-12 induces IgG2c antibody responses by inducing IFNγ production from T cells or NK cells [Gracie et al., Eur. J. Immunol. (1996) 26: 1217-1221].

Ultimately, the inventors have discovered that the combination of K3 CpG and cGAMP has a strong antitumor effect because this combination alone can effectively suppress tumor growth in EG-7 mouse tumor models (FIG. 5). The in vivo results obtained by the inventors show that the combination induces strong $CD8^+$ T cell responses (FIG. 6). In addition, it has been already reported that CpG ODN induces purification of $CD8^+$ cytotoxic T cells [Krieg et al., Nat. Rev. Drug Discov. (2006) 5: 471-84]. Thus, it is possible that the antitumor effect of the combination of the invention is due to the induction of strong $CD8^+$ T cell activation. The inventors' hypothesis is supported by the previous report showing that vaccination of OVA conjugate CpG ODN also has a potent antitumor effect dependent on $CD8^+$ T cells [Cho et al., Nat. Biotechnol (2000) 18: 509-514]. However, the possibility of activation of NK cells enhanced by the combination treatment of the present invention cannot be eliminated. As in the case of hPBMC culture, the inventors identified NK cells as playing a major role in the synergistic effect of IFNγ. The advantage of the combined therapy of the invention over the previously reported CpG based antitumor agents such as OVA conjugate CpG ODN [Cho et al., Nat Biotechnol. (2000) 18: 509-514] or nanoparticle conjugate CpG ODN [De et al., Proc. Natl. Acad. Sci. U.S.A. (2013) 110: 19902-7] is that the combined therapy does not require a chemical conjugation between K3 CpG and cGAMP. Furthermore, unlike these systems, the approach of the present invention does not require injection or conjugation of tumor antigens. This functions as an antigen-free antitumor agent rather than a prophylactic vaccine.

As a conclusion, the studies conducted by the inventors suggest that the combination of a TLR9-agonist and a STING-agonist is a type 1 adjuvant that is advantageous as vaccines requiring strong cellular immune responses and a promising antitumor agent that can also stimulate human NK cells for the synergistic production of IFNγ. Thus, the results obtained by the inventors provide insight into the action mechanism of combining TLR9 and STING signaling pathways, which can potentially promote the immunotherapeutic and adjuvant properties of the combination of the invention.

Example 10: Experiments Related to Multiple Types of STING Ligands

The present Example performs experiments similar to those in Examples 1-9. Similar experiments are conducted using cGAMP, c-di-GMP, 2'3'-cGAMP, and DMXAA and using cGAMP, c-di-GMP, 2'3'-cGAMP, and DMXAA instead of 3'3'-cGAMP under the conditions of Examples 7-9.

In view of the above, it is understood that the same results as 3'3'-cGAMP are obtained with cGAMP, c-di-GMP, 2'3'-cGAMP, and DMXAA as seen in Examples 1-6.

Example 11: Experiments Related to Multiple Types of CpG (Other than K3)

The present Example conducted the experiments in Examples 1-9 using CpG other than K3, such as CpG 1826 and D35 CpG.

(Materials and Methods)

Each of CpG 1826 (SEQ ID NO: 2=5'-tccatgacgttcctgacgtt-3') and D35 CpG (SEQ ID NO: 3=5'-ggtgcatcgatgcagggggg-3') was purchased form Invivogen and were synthesized with Gene Design (Ibaraki, Osaka, Japan). After the synthesis or purchase, they were used by dissolving the lyophilized product thereof with sterilized water.

(Method)

Mouse (c57BL/6) splenocytes were adjusted to $1 \times 10^7$ cells/ml. IFN-γ in the culture supernatant simulated for 24 hours with a stimulant such as the above-described CpG in vitro was measured by ELISA. These methods were performed as described in (General approach).

(Results)

The results are shown in FIG. 12. As shown, it was demonstrated that each CpG, when combined with a STING agonist 3'3'-cGAMP, produces a synergistic effect in interferon production in splenocytes. Thus, it is demonstrated that the action effect of the present invention is exerted broadly by all CpG, and not limited to a specific CpG.

MENTIONED REFERENCES

1. Kawai et al., Immunity. (2011)34: 637-650
2. Trinchieri et al., Nat. Rev. Immunol. (2007) 7: 179-190.
3. Seder et al., Proc. Natl. Acad. Sci. U.S.A (1993) 90: 10188-92.
4. Hsieh et al., Science. (1993) 260: 547-549.
5. Spellberg et al., Clin. Infect. Dis. (2001) 90509: 76-102.
6. Mantovani et al., Curr. Opin. Immunol. (2010) 22: 231-237.
7. Hung et al., J. Exp. Med. (1998) 188: 2357-68.
8. Vesely et al., Annu. Rev. Immunol. (2011) 29: 235-271.
9. Vitale et al., Eur. J. Immunol. (2014) 44: 1582-1592.
10. Hartmann et al., J. Immunol. (2000) 164: 944-953.
11. Wagner et al., Trends Immunol. (2004) 25: 1-6.
12. Krieg et al., Nat. Rev. Drug Discov. (2006) 5: 471-84.
13. Klinman et al., Nat. Rev. Immunol. (2004) 4: 1-10.
14. Desmet et al., Nat. Rev. Immunol. (2012) 12: 479-491.
15. Barber et al., Immunol. Rev. (2011) 243: 99-108.
16. Sun et al., Science. (2013) 339: 786-91.
17. Wu et al., Science. (2013) 339: 826-30.
18. Zhang et al., Mol. Cell. (2013) 51: 226-35.
19. Burdette et al., Nature. (2011) 478: 515-8.
20. Mcwhirter et al., J. Exp. Med. (2009) 206: 1899-1911.
21. Li et al., Science. (2013) 341: 1390-4.22. Tang et al., PLoS One. (2013) 8:1-6.
23. Hogenesch et al., Front. Immunol. (2013) 3:1-13.
24. Macleod et al., Proc. Natl. Acad. Sci. U.S.A (2011) 108:7914-7919.
25. Weeratna et al., Vaccine. (2000) 18: 1755-1762.
26. Verthelyi et al., J. Immunol. (2001) 166: 2372-2377.
27. Hunter et al., Immunol. Lett. (1997) 59: 1-5.
28. Nguyen et al., J. Immunol. (2002) 169: 4279-4287.
29. Kawai et al., Nat. Immunol. (2004) 5: 1061-8.
30. Dubensky et al., Ther. Adv. Vaccines. (2013) 1: 131-143.
31. Way et al., Immunol. (2007) 178: 4498-4505.
32. Krummen et al., J. Leukoc. Biol. (2010) 88: 189-99.
33. Hornung et al., Immunol. (2002) 168: 4531-4537.
34. Chace et al., Clin. Immunol. Immunopathol. (1997) 84: 185-193.
35. Swanson et al., J. Exp. Med. (2010) 207: 1485-500.
36. Chu et al., J. Exp. Med. (1997) 186: 1623-1631.
37. Muller et al., J. Immunol. (1993) 150: 5576-5584.
38. Seki et al., Nat. Med. (2003) 9: 1047-1054.
39. Lin et al., Eur. J. Immunol. (2004) 34: 1483-7.
40. Gracie et al., Eur. J. Immunol. (1996) 26: 1217-1221.
41. Cho et al., Nat. Biotechnol. (2000) 18: 509-514.
42. De et al., Proc. Natl. Acad. Sci. U.S.A (2013) 110: 19902-7.
43. Sauer et al., Infect. Immun. (2011) 79: 688-94.
44. Honda et al., Nature. (2005) 434: 772-777.
45. Kobiyama et al., Proc. Natl. Acad. Sci. U.S.A (2014) 111: 1-6.
46. Kuroda et al., Immunity. (2011) 34: 514-526.

As described above, the present invention is exemplified by the use of its preferred embodiments. However, it is understood that the scope of the present invention should be interpreted solely based on the claims. It is also understood that any patent, any patent application, and any references cited herein should be incorporated herein by reference in the same manner as the contents are specifically described herein. The present application claims priority to Japanese Patent Application No. 2014-235934. The entire content of these applications is incorporated herein by reference.

INDUSTRIAL APPLICABILITY

The present invention appears to have a technical and economical ripple effect as a next-generation adjuvant, such that industrial applicability can be found in the pharmaceutical industry, biotechnology industry, or the like.

SEQUENCE LISTING FREE TEXT

SEQ ID NO: 1: sequence of K3 CpG: 5'-atcgac-tatcgagagttctc-3'
SEQ ID NO: 2: sequence of CpG1826: 5'-tc-catgacgttcctgacgtt-3'
SEQ ID NO: 3: sequence of D35 CpG: 5'-ggtgcatc-gatgcagggggg-3'

The invention claimed is:

1. A method of treating cancer or providing prevention of cancer to a subject by reducing or eliminating a type II immune response and expressing or enhancing a type I immune response, consisting essentially of administering an effective amount of a CpG oligonucleotide and an effective amount of a STING agonist to the subject, wherein the CpG oligonucleotide is a CpG oligonucleotide selected from the group consisting of K3 CpG (SEQ ID NO: 1), CpG 1826 (SEQ ID NO: 2), and D35 CpG (SEQ ID NO: 3) and wherein the STING agonist is a STING agonist selected from cGAMP, 3' 3'-cGAMP, c-di-GAMP, c-di-AMP, 2' 3'-cGAMP, and DMXAA.

2. The method of claim 1, wherein the cancer is selected from lymphoma and melanoma.

3. The method of claim 1 wherein the treatment or prevention is achieved by inducing interferon γ(IFN-γ).

4. The method of claim 1 wherein the treatment or prevention is achieved by a vaccine adjuvant.

5. The method of claim 1, wherein the treatment or prevention is achieved by reducing or eliminating IgE inducing action of a STING agonist.

6. The method of claim 1, wherein the CpG oligonucleotide is a type KB oligonucleotide.

7. A method of exerting a type I adjuvant effect of a STING agonist for treating or preventing cancer, consisting essentially of administering the STING agonist in conjunction with a CpG oligonucleotide, wherein the CpG oligonucleotide is a CpG oligonucleotide selected from the group consisting of K3 CpG (SEQ ID NO: 1), CpG 1826 (SEQ ID NO: 2), and D35 CpG (SEQ ID NO: 3) and wherein the STING agonist is a STING agonist selected from cGAMP, 3' 3'-cGAMP, c-di-GAMP, c-di-AMP, 2' 3'-cGAMP, and DMXAA.

8. A method of enhancing action of a type I adjuvant of a CpG oligonucleotide for treating or preventing cancer, consisting essentially of administering the CpG oligonucleotide in conjunction with a STING agonist, wherein the CpG oligonucleotide is a CpG oligonucleotide selected from the group consisting of K3 CpG (SEQ ID NO: 1), CpG 1826 (SEQ ID NO: 2), and D35 CpG (SEQ ID NO: 3) and wherein the STING agonist is a STING agonist selected from cGAMP, 3' 3'-cGAMP, c-di-GAMP, c-di-AMP, 2' 3'-cGAMP, and DMXAA.

* * * * *

UNITED STATES PATENT AND TRADEMARK OFFICE
CERTIFICATE OF CORRECTION

PATENT NO. : 11,058,758 B2
APPLICATION NO. : 15/528002
DATED : July 13, 2021
INVENTOR(S) : Ken Ishii et al.

Page 1 of 1

It is certified that error appears in the above-identified patent and that said Letters Patent is hereby corrected as shown below:

In the Claims

Column 40, Claim 6, Line 15:
"type KB oligonucleotide." should read: -- type K/B oligonucleotide. --

Signed and Sealed this
Fifth Day of July, 2022

Katherine Kelly Vidal
*Director of the United States Patent and Trademark Office*

SEQUENCE LISTING

```
<160> NUMBER OF SEQ ID NOS: 3

<210> SEQ ID NO 1
<211> LENGTH: 20
<212> TYPE: DNA
<213> ORGANISM: artificial sequence
<220> FEATURE:
<223> OTHER INFORMATION: synthetic oligonucleotide K3 CpG

<400> SEQUENCE: 1
atcgactctc gagcgttctc                                                   20

<210> SEQ ID NO 2
<211> LENGTH: 20
<212> TYPE: DNA
<213> ORGANISM: artificial sequence
<220> FEATURE:
<223> OTHER INFORMATION: synthetic oligonucleotide CpG1826

<400> SEQUENCE: 2
tccatgacgt tcctgacgtt                                                   20
```

```
<210> SEQ ID NO 3
<211> LENGTH: 20
<212> TYPE: DNA
<213> ORGANISM: artificial sequence
<220> FEATURE:
<223> OTHER INFORMATION: synthetic oligonucleotide D35 CpG

<400> SEQUENCE: 3
ggtgcatcga tgcagggggg                                              20
```